United States Patent [19]

Hovda

[11] Patent Number: 5,587,500
[45] Date of Patent: Dec. 24, 1996

[54] SULFONATION OF FATTY ACID ESTERS

[75] Inventor: Keith D. Hovda, Kent, Wash.

[73] Assignee: The Chemithon Corporation, Seattle, Wash.

[21] Appl. No.: 123,448

[22] Filed: Sep. 17, 1993

[51] Int. Cl.$^6$ .................................................. C11D 1/28
[52] U.S. Cl. ............................................................ 554/98
[58] Field of Search ................................................ 554/98

[56] References Cited

U.S. PATENT DOCUMENTS

| | | | |
|---|---|---|---|
| 1,926,442 | 9/1933 | Gunther et al. | 260/112 |
| 2,195,145 | 3/1940 | Crittenden | 260/400 |
| 2,195,186 | 3/1940 | Moyer | 260/400 |
| 2,195,187 | 3/1940 | Moyer | 260/400 |
| 2,195,188 | 3/1940 | Moyer | 260/400 |
| 2,271,619 | 2/1942 | Bradshaw et al. | 260/410 |
| 2,460,968 | 2/1949 | Bert et al. | 260/400 |
| 2,628,253 | 2/1953 | Dowdall | 260/545 |
| 2,647,925 | 8/1953 | Gilbert et al. | 260/513 |
| 2,785,193 | 3/1957 | Blaser et al. | 260/465.1 |
| 2,806,055 | 9/1957 | Feighner | 260/505 |
| 2,822,387 | 2/1958 | Bloch | 260/513 |
| 2,829,975 | 4/1958 | Popeck et al. | 96/55 |
| 2,841,606 | 7/1958 | Hechenbleikner et al. | 260/461 |
| 2,915,473 | 12/1959 | Stirton et al. | 252/161 |
| 2,951,809 | 9/1960 | Nelson | 252/33 |
| 2,974,152 | 3/1961 | Schulze et al. | 260/400 |
| 3,117,928 | 1/1964 | Thylefors | 233/20 |
| 3,142,691 | 7/1964 | Wulff et al. | 260/400 |
| 3,158,632 | 11/1964 | Blaser et al. | 260/400 |
| 3,159,657 | 12/1964 | Wulff et al. | 260/400 |
| 3,169,142 | 2/1965 | Knaggs et al. | 260/457 |
| 3,251,868 | 5/1966 | Stein et al. | 260/400 |
| 3,256,303 | 6/1966 | Stein et al. | 260/400 |
| 3,259,645 | 7/1966 | Brooks et al. | 260/459 |

(List continued on next page.)

FOREIGN PATENT DOCUMENTS

| | | |
|---|---|---|
| 0173941 | 3/1986 | European Pat. Off. . |
| 2571368 | 4/1986 | France .................. C07C 143/12 |
| OS 1418887 | 9/1969 | Germany . |
| PS 1418887 | 12/1971 | Germany . |
| 3123681 | 3/1982 | Germany . |
| 3334517 | 4/1984 | Germany . |
| 59-25369 | 2/1984 | Japan .................. C07C 143/12 |
| 1475757 | 6/1977 | United Kingdom . |

OTHER PUBLICATIONS

Chemical Abstracts, vol. 116, #4, 1992, p. 121, 23170h.

Okumura, O., Sakatani, T., and Jaman, I., Tr–Meshdunar, "Mechanism of Sulfonation of Fatty Acid Esters with Sulfur Trixoide and Properties of Alpha–Sulfo Fatty Acid Esters," Proceeding of the 7th International Congress on Surface Active Agents in Moscow, vol. 1, pp. 224–237 (1976).

Smith, F. D. and Stirton, A. J., "The Alpha–Sulfonation of Alkyl Palmitates and Stearates," JAOCS, vol. 44, p. 45 (1967).

European Search Report mailed Dec. 5, 1994 in EP Application No. 94 11 4562.5.

Abstract for AN 75–54597W & JP–A–49 123 474; Mitsubishi Gas Chem. Ind. (Derwent Publications, Ltd; Week 7533). (1988).

Patent Abstracts of Japan, vol. 8 No. 110 for JP–A–59 025 369; "Method for Bleaching Ester of § May 23, 1984".

Primary Examiner—Gary Geist
Assistant Examiner—Deborah D. Carr
Attorney, Agent, or Firm—Marshall, O'Toole, Gerstein, Murray & Borun

[57] ABSTRACT

A sulfonation process includes the process steps of air sulfonating a fatty acid alkyl ester feedstock, bleaching the crude product with co-addition of up to about 40 wt. % of an alcohol based upon the weight of the crude product. The bleaching/alcohol addition step of the process is performed in a nonmetallic or low-iron alloy system at temperatures above 90° C. The resulting product is then neutralized with a liquid base or metal carbonate.

65 Claims, 10 Drawing Sheets

U.S. PATENT DOCUMENTS

| | | | |
|---|---|---|---|
| 3,274,117 | 9/1966 | Stein et al. | 252/161 |
| 3,328,460 | 6/1967 | Mey | 260/505 |
| 3,338,838 | 8/1967 | Wilson | 252/161 |
| 3,345,301 | 10/1967 | Stein et al. | 252/152 |
| 3,350,428 | 10/1967 | Brooks et al. | 260/400 |
| 3,351,559 | 11/1967 | Stein et al. | 252/138 |
| 3,354,187 | 11/1967 | Steen et al. | 260/400 |
| 3,377,290 | 4/1968 | Stein et al. | 252/152 |
| 3,390,096 | 6/1968 | Stein et al. | 252/161 |
| 3,427,342 | 2/1969 | Brooks et al. | 260/458 |
| 3,839,391 | 10/1974 | Susuki et al. | 260/457 |
| 3,925,441 | 12/1975 | Toyoda et al. | 260/458 |
| 3,997,575 | 12/1976 | Oghoshi et al. | 260/400 |
| 3,997,576 | 12/1976 | Oghoshi et al. | 260/410.9 |
| 4,036,596 | 7/1977 | Ogoshi et al. | 23/283 |
| 4,080,372 | 3/1978 | Stein et al. | 260/400 |
| 4,303,590 | 12/1981 | Tanaka et al. | 260/410.9 |
| 4,404,143 | 9/1983 | Sekiguchi et al. | 260/400 |
| 4,438,025 | 3/1984 | Satsuki et al. | 252/545 |
| 4,547,318 | 10/1985 | Kloetzer et al. | 260/400 |
| 4,671,900 | 6/1987 | Schmid et al. | 260/400 |
| 4,695,409 | 9/1987 | Piorr et al. | 260/400 |
| 4,820,451 | 4/1989 | Piorr et al. | 260/400 |
| 5,118,440 | 6/1992 | Cutler et al. | 252/174.17 |

SULFONATION OF FATTY ACID ESTERS

BACKGROUND OF THE INVENTION

1. Field of the Invention

The invention relates generally to the sulfonation of fatty acid esters and derivatives thereof and, more particularly, the invention relates to methods of sulfonation of fatty acid esters and of bleaching and neutralizing the resulting sulfonated product.

2. Description of Related Technology

The sulfonates of fatty acids and fatty acid derivatives are commercially valuable as wetting agents and detergent components due to their excellent surface-active properties and resistance to hard water. A sulfonation process which includes reacting excess gaseous sulfur trioxide with fatty acids or fatty acid derivatives to produce a sulfonic acid is well known in the art. Because the sulfonic acid containing product resulting from such a process is typically dark in color and therefore undesirable for commercial use, it is also known to bleach the product, for example, by treatment with hydrogen peroxide. The bleached product is then typically neutralized with sodium hydroxide.

The known bleaching processes are limited in several ways. For example, prior experiments teach that the bleaching process should be performed at a temperature of 90° C. or less. Typically, a bleaching temperature between about 70° C. and about 80° C. has been utilized. For example, in an experiment where methylester sulfonic acid was reacted with hydrogen peroxide in stainless steel equipment, heating the bleaching system above 75° C. resulted in product having a darker color than product bleached at lower temperatures. Operation at higher temperatures resulted in a rapid exotherm and the total consumption of hydrogen peroxide. Once all the hydrogen peroxide was consumed, the color of the acid increased with time.

The prior art teaches that the sulfonation and bleaching processes may be improved by adding an aliphatic alcohol to the reaction mixture. For example, Ogoshi, et al., U.S. Pat. No. 3,997,575 (Dec. 14, 1976) discloses utilizing up to about twenty weight percent alcohol in a sulfonic acid bleaching process. Although the use of a higher percentage of alcohol would seem to be desirable because the alcohol decreases the viscosity of the reaction mixture, thereby guarding against undesirable localized temperature increases which occur in a more viscous mixture, it has generally been taught that a higher amount of alcohol is undesirable for several reasons, including difficulties in removing free alcohol from the neutralized product and the unpleasant odor of the alcohol which necessitates deodorization of the product.

The known bleaching processes (and corresponding neutralization processes) often produce undesirable by-products in addition to the desirable lighter-colored reaction product. For example, the neutralized product may include unreacted hydrogen peroxide, oxygen from the decomposition of hydrogen peroxide, dimethyl ether or other ethers and possibly organic peroxides. These materials can present hazards in downstream storage and processing.

Another challenge faced in the preparation of sulfonates of fatty acids and fatty acid derivatives is to produce a highly active sulfonate paste (i.e. having greater than 55 wt. % of the surface-active neutralized sulfonate) and a low yield of undesirable by-product di-salt (less than 6 wt. %). In the past, neutralization with metal hydroxides and water were easily performed at active concentrations of up to about 35 wt. %, but attempts to produce higher active concentrations also produced a very high di-salt yield. Also, previously, the sensitivity of the continuous neutralization process to factors such as alcohol concentration, neutralization temperature and neutralization pH was not known.

SUMMARY OF THE INVENTION

It is an object of the invention to overcome one or more of the problems described above.

According to the invention, a sulfonation process is provided which comprises the process steps of sulfonating a fatty acid alkyl ester feedstock, bleaching the crude product and then neutralizing the resulting product. The process is accomplished by employing one or more of the following expedients:

In a first expedient, the bleaching step of the inventive process is performed in a non-metallic or low-iron corrosion resistant alloy. By utilizing such equipment, bleaching temperatures above 90° C. are successfully employed.

In a second expedient, the bleaching operation is performed with the co-addition of at least about 21 wt. % alcohol based upon the crude sulfonic acid weight.

In a third expedient, the neutralization step is performed uitilizing a solid base in a solution or slurry of alcohol.

Other objects and advantages of the invention will be apparent to those skilled in the art and from the following detailed description, taken in conjunction with the drawing and the appended claims.

DETAILED DESCRIPTION OF THE INVENTION

Process Overview

Figure 1:
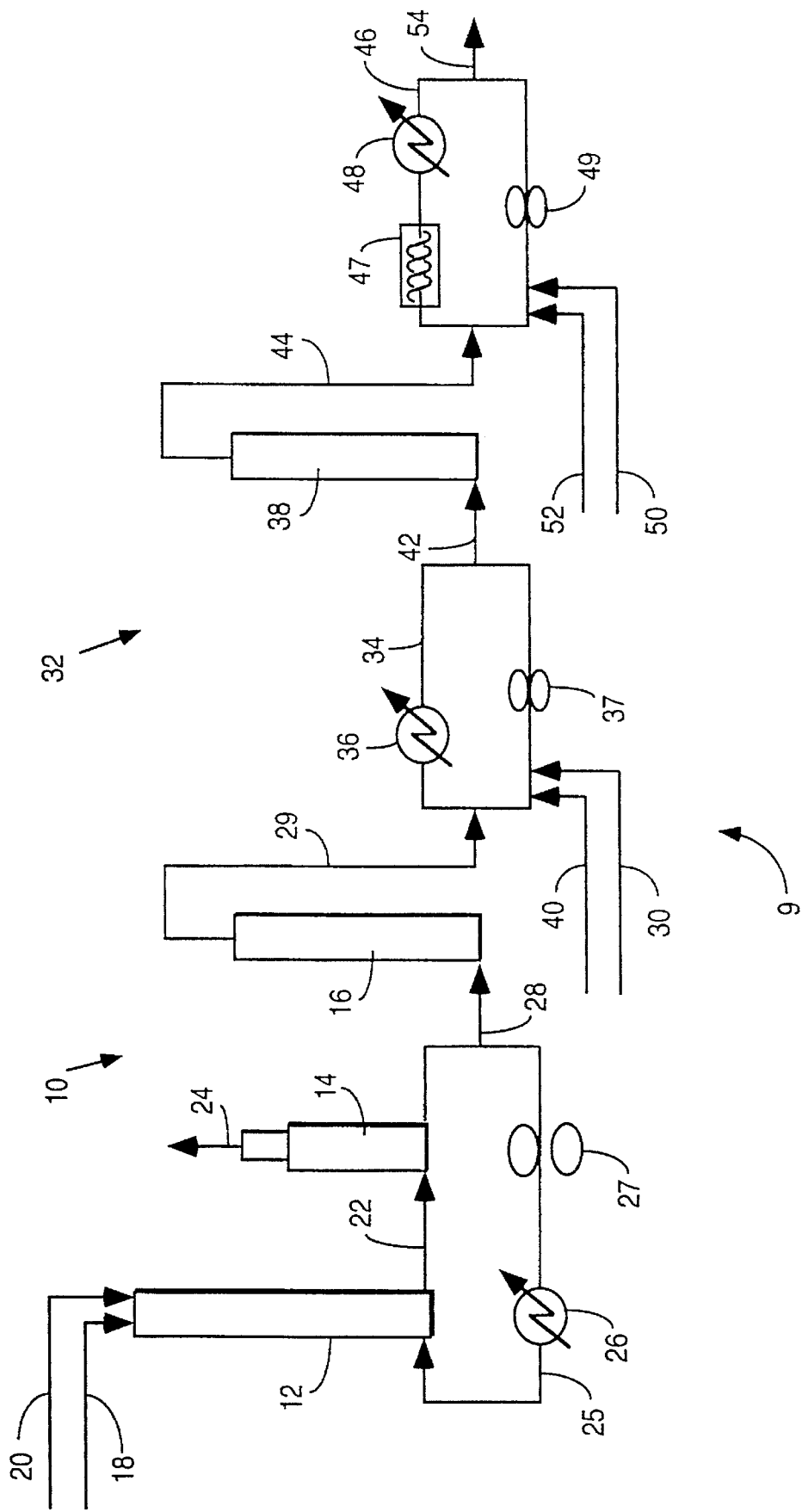
FIG. 1 is a process flow diagram illustrating a sulfonation process according to the invention, including bleaching with plug flow digestion and neutralization with a liquid base.

With reference to FIG. 1, the invention comprises the process steps of air sulfonating a fatty acid alkyl ester feedstock and bleaching and neutralizing the resulting product in a continuous process system generally designated 9. The sulfonation portion of the system 9, generally designated 10, may include a falling film reactor 12, a cyclone 14 for disengaging liquid and gas streams, and a digester 16. Feedstock is fed from a conduit 18 and an air/$SO_3$ mixture from a conduit 20 into the reactor 12. A reaction mixture exits the reactor 12 through a conduit 22 and enters the cyclone 14 where disengaged gas is directed through a vent 24. A recycle stream of the reaction liquid is fed from the cyclone 14 into the reactor 12 through a conduit 25 having a heat exchanger 26 and a pump 27.

Reaction liquid from a recycle outlet 28 is fed to the reactor 16 where acid digestion occurs. The crude acid is then transported through a conduit 29 and is introduced along with a bleaching agent from a conduit 30 into a non-metallic bleaching system, generally designated 32, which may include a recycle loop 34 having a heat exchanger 36 and a pump 37. The bleaching system 32 may also include a digester 38. The bleaching agent may be a peroxide, preferably hydrogen peroxide or ozone.

In addition to the bleaching process, a further reaction step is performed in the bleaching system 32 which comprises the addition of an alcohol from a conduit 40 to the reaction mixture in the loop 34. The alcohol may be a primary or secondary alcohol having 1–4 carbon atoms, or mixtures thereof, preferably ethanol and/or methanol. Methanol is particularly preferred. Alcohol amounts of up to about 40 wt. % based upon the crude sulfonic acid are preferred. Product exiting an outlet recycle conduit 42 may then be digested in the bleach digester 38.

The bleaching and final reaction steps in the system 32 are preferably performed at temperatures above 90° C. Particularly preferred operating temperatures range up to about 110° C.

Finally, the product exiting from the digester 38 through a conduit 44 is neutralized. A neutralization step according to the inventive process may be performed with a liquid or a solid base. A liquid base as defined herein may be aqueous or non-aqueous. As illustrated in FIG. 1, a neutralizing system 46 utilizing a liquid base includes an in-line mixer 47, a heat exchanger 48, and a pump 49. A liquid base from a conduit 50, such as sodium hydroxide and water, if necessary, from a conduit 52, are fed into the system 46 which is a reactor loop with the final product leaving the system through a conduit 54. Alternatively, in a preferred process according to the invention, a metal carbonate, preferably sodium carbonate is utilized for the neutralization process.

Description of Chemistry

Although not intended to be limiting, the following mechanism for the sulfonation process (and side reactions) as proposed by Smith, F. D. and Stirton, A. J., "The Alpha-Sulfonation of Alkyl Palmitates and Stearates," JAOCS, Vol. 44, page 45 (1967) and confirmed by Okumura, O., Sakatani, T., and Jaman, I., Tr-Meshdunar, "Mechanism of Sulfonation of Fatty Acid Esters with Sulfur Trixoide and Properties of Alpha-Sulfo Fatty Acid Esters," Proceedings of the 7th International Congress on Surface Active Agents in Moscow, Vol. 1, pages 224–37 (1976) are believed helpful for an understanding of the details of the inventive process.

As described above with respect to FIG. 1, the first step of the inventive process comprises air sulfonating a fatty acid ester feedstock having the formula:

$RCH_2COOR_1$ 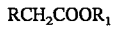

wherein R is $C_4$ to $C_{22}$ ($C_{10}$ to $C_{18}$ alkyl is preferred), $R_1$ is $C_1$ to $C_8$ ($C_1$ and $C_2$ are preferred).

The initial addition of sulfur trioxide to a fatty acid ester, for example, a methylester (I) as shown in the reaction below, forms an intermediate (II) which may be a mixed anhydride, or an adduct, but which is definitely not a sulfonate:

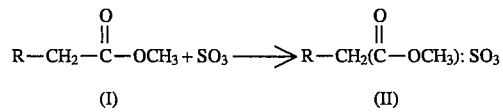

The formation of the intermediate (II) activates the carbon atom alpha to the carbonyl, which allows free $SO_3$ to react to form another intermediate (III) as shown below that is both a sulfonate and a sulfur trioxide adduct or mixed anhydride:

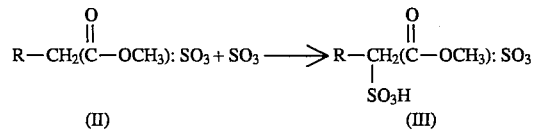

The intermediate (III) undergoes slow elimination of $SO_3$ to form the alpha-sulfomethylester (IV) and free $SO_3$. The released $SO_3$ is then available to react with either the fatty methylester (I) or the intermediate (II) in a final step:

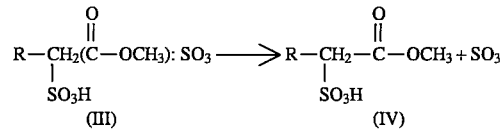

The above-step is rate controlling. To achieve commercially feasible reaction rates, sufficient excess $SO_3$ must be added to produce significant amounts of the intermediate (III) which slowly produces the required free $SO_3$ to drive the sulfonation reaction to completion. Therefore, the mole ratio of feedstock to $SO_3$ in the reaction mixture preferably is about 1:1.1 to about 1:1.5 (most preferably about 1:1.1 to about 1:1.3).

Other byproduct reactions, such as the formation of color bodies, or the reduction of $SO_3$ to form $SO_2$ and an olefin, or the possible formation of sultones from internal olefins also consumes $SO_3$. Therefore, at least a mole ratio of 1.1 $SO_3$ per mole of the fatty methylester is required to achieve levels of sulfonation of greater than 90%.

Once acceptable levels of sulfonation have occurred, large amounts of intermediate (III) are still present. Allowing the intermediate (III) to react by the elimination of $SO_3$ would require a great amount of time, and would result in very large amounts of byproduct reactions because of the high level of $SO_3$ that would be present. To reduce the byproduct reactions and greatly reduce the processing time, an alcohol, most preferably methanol, is added to the reaction mixture in order to quickly react with excess $SO_3$ and produce the desired alpha-sulfo methylester acid and hydrogen methyl sulfate by the following reaction:

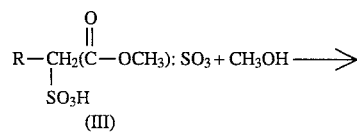

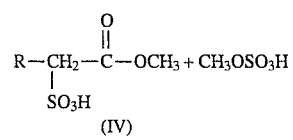

The quality of the final product during and after sulfonation is typically measured by color, and extractable oil, volatile oil, methylester sulfonic acid (IV), and intermediate (III) concentration. Researchers have found that the intermediate (III) forms a hydrolysis product by cleavage of the ester bond upon neutralization as shown in the following equation:

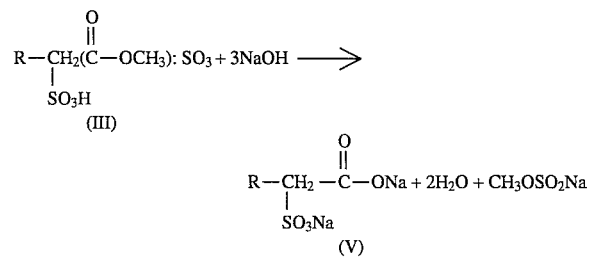

The material (V) is an undesirable di-salt of a sulfonate and a carboxylate, or alpha-sulfocarboxylic acid (ASCA).

The structure of the color bodies formed during the by-product reactions is becoming better understood. Conjugation of double bonds and large electron rich substituents such as sulfonic acids, sultones and the carbonyl group may be responsible for the strong light absorption. Bleaching of the product with hydrogen peroxide is consistent with the epoxidation of an olefin, followed by hydrolysis to a glycol. Hydrogen peroxide is also susceptible to a variety of decomposition reactions resulting in the formation of water and oxygen.

The presence of water during the bleaching step also may cause hydrolysis of the methylester sulfonic acid, or any of its intermediates. When methylester sulfonic acid is hydrolyzed, a sulfonated carboxylic acid, or di-acid (VI) is formed pursuant to the following reaction:

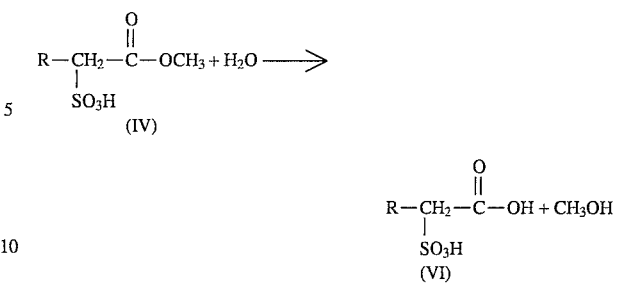

Hydrolysis is mitigated because some of the water present reacts with free $SO_3$ to form sulfuric acid, and the excess methanol present drives the reverse reaction, reesterfication. When analyzed in the acid form the di-acid (VI) may be indistinguishable from the intermediate (III). Both (VI) and (III) will form the di-salt (V) upon neutralization.

Not only reactions involving methylesters occur in the bleaching system. The hydrogen methyl sulfate formed by the reaction of methanol with free $SO_3$, or with the intermediate (III) can react with methanol to form dimethyl sulfate according to the following:

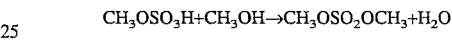

$$CH_3OSO_3H + CH_3OH \rightarrow CH_3OSO_2OCH_3 + H_2O$$

The dimethyl sulfate can further react with methanol to form hydrogen methyl sulfate and dimethyl ether according to the following reaction:

$$CH_3OSO_2OCH_3 + CH_3OH \rightarrow CH_3OSO_3H + CH_3OCH_3$$

The hydrogen methyl sulfate can then react again, repeating the cycle. The reaction is stopped when one of the reagents is exhausted, or when the reaction is cooled and neutralized. Dimethyl ether has been observed in neutral MES.

The di-salt (V) can also be formed by hydrolysis of methylester sulfonic acid (IV) or the neutral salt in the presence of a base such as sodium hydroxide according to the following:

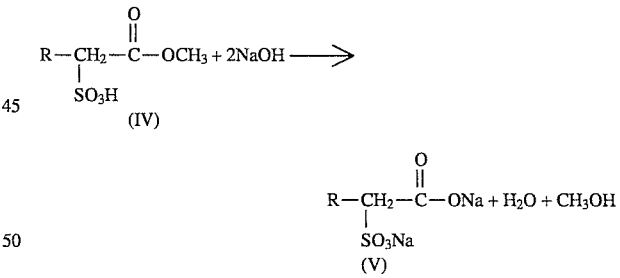

The hydrolysis rate is much higher at pH levels above 9 and at elevated temperatures (see W. Stein and H. Baumann, "Sulfonated Fatty Acids and Esters: Manufacturing Process, Properties and Applications" JOACS, Vol. 52, page 327 (September 1975)). Very rapid and intimate mixing of the sulfonic acid and base streams are required during neutralization to avoid creating high local pH values and high temperatures that can lead to excessive hydrolysis.

It is advantageous to use a metallic carbonate such as sodium carbonate according to the inventive process because sodium carbonate is a weaker base than sodium hydroxide. It also produces one half as much water of neutralization, and has a much lower heat of neutralization. When methylester sulfonic acid (IV) is neutralized with sodium carbonate to form the neutral methylester sulfonate, sodium alpha-sulfomethylester as SASME (VII), according to the following reaction, all the conditions that lead to hydrolysis are reduced.

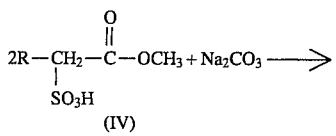
(IV)

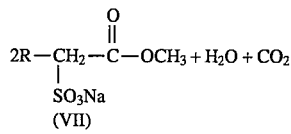
(VII)

Sulfonation

With reference to FIG. 1, the initial sulfonation step of a process according to the invention is preferably air sulfonation utilizing a falling film reactor 12 and a digester 16. Approximately 75% of the sulfonation is accomplished in the falling film reactor 12. The digester 16 is preferably a baffled plug flow reactor which is temperature controlled and constructed from suitable materials, such as stainless steel.

A preferred sulfonation reaction according to the invention takes into account the relationship between digestion conditions and the neutral product which previously have not been defined in the literature. It has been found that there is only a weak relationship between the severity of the digestion conditions and the color of the neutral product or the yield to the undesirable byproduct di-salt. However, as more fully described with respect to Example 5 below, there appears to be a statistically significant relationship between petroleum ether extractable (PEE) oils present in the crude product following the acid digestion step and the PEE oils in the neutral product prepared according to the invention.

It has been found that the acid PEE and the final neutral PEE go through a minimum as the digestion time and temperature are increased, with the neutral PEE being consistently lower than the PEE level in the digested acid. In fact, the PEE level in the digested acid has been found to be approximately twice that of the PEE level in the neutral produce prepared according to the invention. Thus, selecting the severity of sulfonation based on the extractable oil in the digested acid is not critical to the process and in fact could lead to unnecessarily high colors and potentially lower yield.

Thus, the sulfonation and subsequent digestion steps should be controlled to produce a final neutral product with sufficiently low free oil for the desired application, and with the highest yield, lowest color and lowest $SO_3$ use.

With the above-described relationships taken into consideration, a preferred sulfonation step according to the invention comprises reacting a methylester feedstock having an iodine value of less than 0.5 with $SO_3$ at a mole ratio of about 1:1.5 (particularly preferred feedstock to $SO_3$ ratio of about 1:1.25), followed by plug flow digestion at about 80° C. to about 95° C. (particularly preferred temperature of about 85° C.) for about 30 minutes.

Bleaching and Alcohol Addition

The bleaching and alcohol addition steps of the inventive process may be performed continuously utilizing a reaction loop and plug flow digester as shown in FIG. 1. The bleaching reaction may also be performed in a semi-batch (see FIG. 2) or continuous (see FIG. 3) reaction in which gaseous by-products are continuously stripped with refluxing methanol. Whether the bleaching process is continuous or semi-batch, the surfaces of the bleaching equipment which are wetted by the crude sulfonic acid are made from non-metallic or low-iron alloy material.

The increase in operating temperature made possible by the non-metallic construction of the bleaching system has been found to reduce the bleaching times required to achieve a product of commercially desirable color from 4 to 16 hours to about 45 minutes to 2 hours. For example, it has been found that bleaching in the presence of passivated 316 stainless steel (SS) at temperatures of 80° C. or higher results in the rapid decomposition of hydrogen peroxide without a significant decrease in color.

Operation at lower temperatures with passivated 316 SS will produce a product with acceptable color, but a very long (greater than four hours) bleaching time is required. In contrast, substituting polymer coated equipment (e.g. TEFLON®) and low iron alloys (e.g. HASTELLOY alloy C) for the 316 SS allows operation of up to at least 110° C. while reducing the four-hour bleaching time to about 1 hour or less. Bleaching temperatures of above 110° C. are possible and may be desirable in certain instances. However, with increasing operating temperatures, the amount of undesirable di-salt also appears to increase.

The most desirable bleaching performance has been obtained with a bleaching solution having a high concentration of hydrogen peroxide (i.e. containing as little water as possible). Therefore, a bleaching solution having a hydrogen peroxide concentration of at least about 50 wt. % is preferred. (Unless otherwise noted, all percentages disclosed herein are with reference to weight percent).

A preferred bleaching process according to the invention comprises about 1 to about 4 wt. % active addition (about 3 wt. % is particularly preferred) of 50% hydrogen peroxide and about 20 wt. % to about 40 wt. % (particularly preferred about 30 wt. %) active addition of alcohol, preferably methanol, along with the digested sulfonic acid from the digester 16. The additions are based on a sulfonic acid weight basis, which is the same as the sum of the fatty acid ester and sulfur trioxide feeds.

The value of alcohol addition is understated in the literature. It has been found that alcohol levels of 40% or more reduce the formation of byproduct di-salt in the bleaching operation and in the subsequent neutralization step. For example, increasing the level of methanol addition in a process from 20% to 30% was found to reduce the level of di-salt in a neutral product from about 8.5% to about 5.5%.

Increasing methanol addition during bleaching also reduces the viscosity of the reaction mixture, which improves heat transfer in a plug flow digester which may be utilized for the bleaching process (see FIG. 1). Higher levels of methanol addition also reduce reaction mixture foaming when bleaching is accomplished utilizing refluxing (see FIGS. 2 and 3). Furthermore, when the neutralization step is performed utilizing a metal carbonate, methanol allows for desirable vapor disengagement.

The inventive process may be performed with alcohol addition of greater than 40 wt. %. However, because higher alcohol addition results in increased operating costs, it does not appear desirable.

With reference to FIG. 1, the bleaching and final reaction (alcohol addition) steps may occur in two stages. The first stage is performed in the dominant bath bleaching loop 34 which is a non-metallic recirculation loop. The loop 34 is preferably constructed from plastic or graphite and includes a non-metallic or low iron, high alloy (e.g. HASTELLOY alloy C) heat exchanger 36. The reactants from conduits 28, 30 and 40 are continuously metered into the loop 34 with the majority of the bleaching and conversion to sulfonic acid occurring quickly. The second stage of the bleaching reaction is performed in the plug flow reactor 38, which is also non-metallic and equipped with heat transfer surfaces to control the reaction temperature of the exothermic reaction.

If a bleaching loop and plug digester as shown in FIG. 1 are used for the bleaching process, the preferred temperature in the bleaching loop 34 ranges from about 70° C. to about 85° C. A preferred operating temperature range for a plug flow digester 38 of a bleaching system according to the invention is about 91° C. to about 110° C. (particularly preferred about 98° C. to about 102° C.). About 80% of the color reduction occurs in the loop 34 along with a very rapid release of energy.

Figure 2:
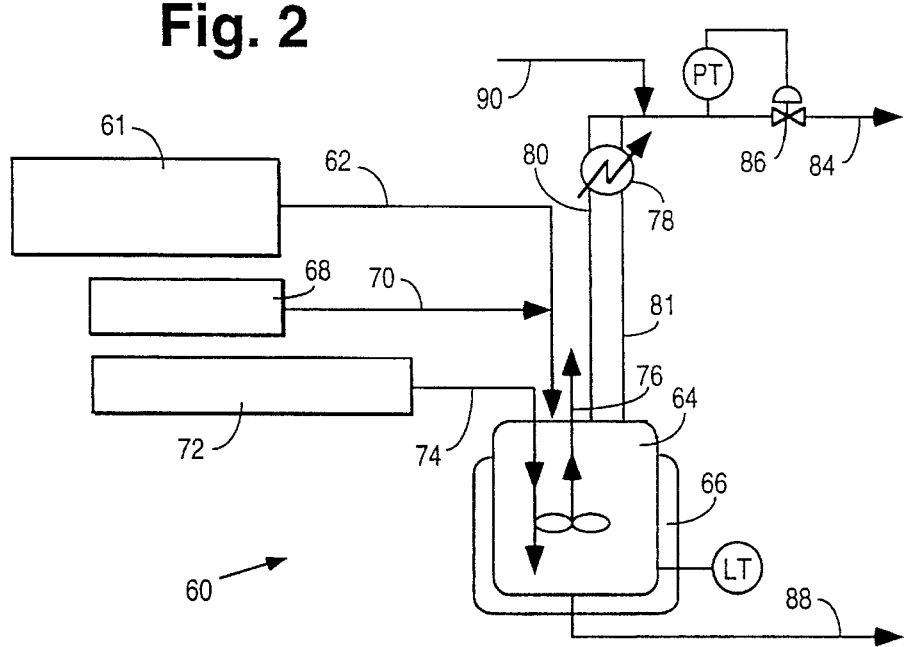
FIG. 2 is a process flow diagram illustrating a semi-batch bleaching process step according to the invention in which gaseous by-products are continuously stripped with refluxing methanol.

A semi-batch bleaching process according to the invention in which gaseous by-products are continuously stripped with refluxing methanol is illustrated in FIG. 2 by a system generally designated 60. A reaction mixture from a sulfonation and digestion process as described with respect to FIG. 1 and represented by a box 61 flows through a conduit 62 and into a pressurized reactor vessel 64. A heating jacket 66 or tracing surrounds the vessel 64 and provides a fixed minimum heat input to the vessel 64. A source of alcohol 68 is also provided to the vessel 64 by a conduit 70 which connects the alcohol source 68 with the conduit 62 through which the reaction mixture flows. A source of hydrogen peroxide 72 is also provided directly to the vessel 64 through a conduit 74. The system 60 includes a mixer 76 located in the vessel 64, a reflux condenser 78 flow connected to the vessel 64 via conduits 80 and 81. Off-gasses are removed from the system 60 through a vent 84 controlled by a valve 86. The reaction mixture exits the system 60 via a conduit 88 flow connected to the vessel 64.

The jacket 66 provides a fixed minimum heat input to the vessel 64 thereby providing a minimum alcohol reflux to guarantee that oxygen concentrations are always below about 5% during the bleaching operation. The refluxing alcohol provides cooling to the reaction mixture and continuously strips by-products therefrom.

Start-up and shut-down of the process requires purging with an inert gas. For this purpose, carbon dioxide produced during a carbonate neutralization step according to the inventive process or other suitable strip gas is added to the vessel. The pressure in the reactor vessel 64 is controlled to maintain the desired temperature in the reaction mixture. An inert gas is also added via a conduit 90 which connects to the system 60 at a discharge of the condenser 78 to prevent an explosive mixture from forming in the vicinity of the condenser. Carbon dioxide from the carbonate neutralization, or another inert gas source, such as nitrogen, or even an oxygen deficient off-gas from the sulfonation reactor would be suitable for addition through the conduit 90.

The operation temperature of a semi-batch bleaching step according to the invention as shown in FIG. 2 ranges from between about 90° C. and about 110° C. with a temperature range of about 98° C. to about 105° C. being preferred. Refluxing allows for very efficient heat transfer, near isothermal operating conditions and thus higher operation temperatures than the loop bleaching process described with respect to FIG. 1.

In the system 60 shown in FIG. 2, all of the bleaching equipment which is wetted by the reaction mixture is made from non-metallic or low-iron alloy material. However, the equipment is otherwise less expensive than the loop and plug digestion equipment required for the process according to the invention as shown in FIG. 1 because heat transfer for the very exothermic bleaching reaction is provided in a condenser 78 and vent system which may be made from stainless steel. For small plants, the combination of semi-batch bleaching and neutralization would be very economical as compared to a continuous process.

Figure 3:
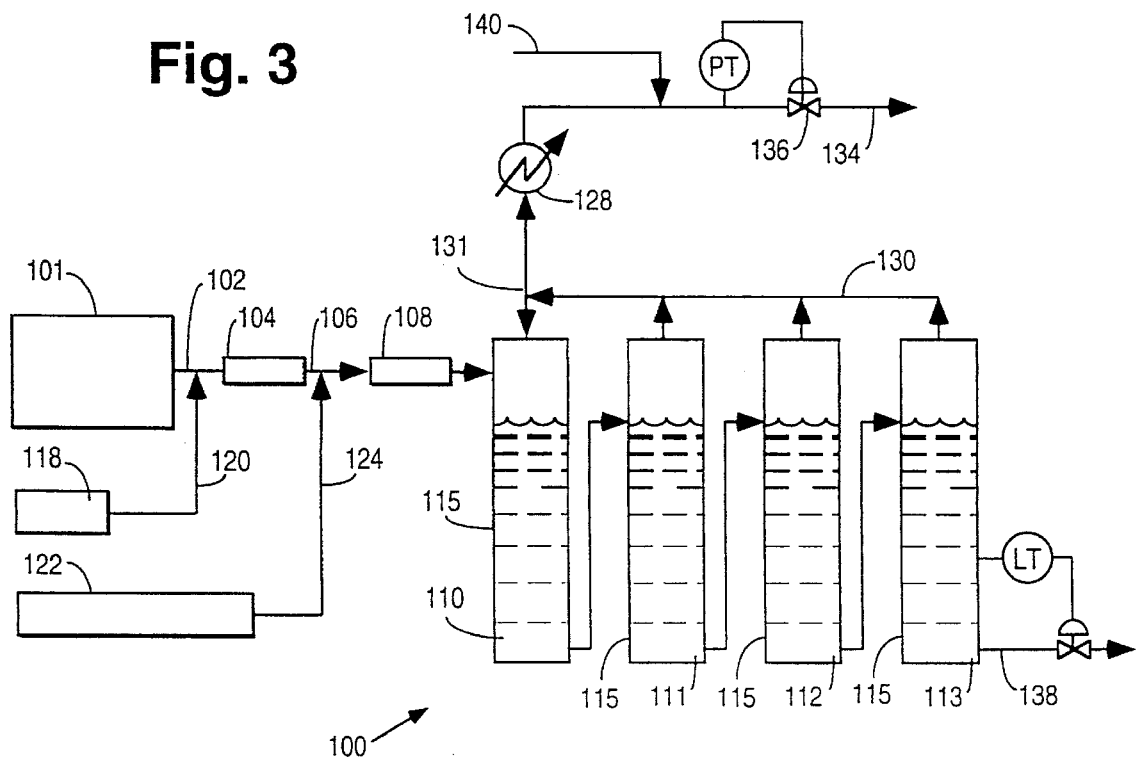
FIG. 3 is a process flow diagram illustrating a continuous bleaching process step according to the invention in which gaseous by-products are continuously stripped.

A continuous bleaching process according to the invention in which gaseous by-products are continuously stripped with refluxing methanol is illustrated in FIG. 3 by a system generally designated 100. A reaction mixture from a sulfonation and digestion process as described with respect to FIG. 1 and represented by a box 101 flows through a conduit 102 through a mixer 104, a conduit 106, a second mixer 108 and into a series of flow connected pressurized reactor vessels 110, 111, 112 and 113. A heating jacket or tracing 115 surrounds each of the vessels 110–113 and provides a fixed minimum heat input thereto. A source of alcohol 118 is also provided to the vessels 110–113 via a conduit 120 which connects the alcohol source 118 with the conduit 102 through which the reaction mixture flows. A source of hydrogen peroxide 122 is also provided to the vessels 110–113 via a conduit 124 which flow connects with the conduit 106. Thus, the reaction mixture and alcohol are mixed in the mixer 104 and then mixed with hydrogen peroxide in the mixer 108.

The system 100 includes a reflux condenser 128 flow connected to the vessels 110–113 via conduits 130 and 131. Alcohol is returned to the vessel 110 via conduit 131. Off-gasses are removed from the system 100 through a vent 134 controlled by a valve 136. The reaction mixture exits the system 100 via a conduit 138 flow connected to the vessel 113.

The jackets 115 provide a fixed minimum heat input to the vessels 110–113 thereby providing a minimum alcohol reflux to guarantee that oxygen concentrations are always below about 5% during the bleaching operation. The refluxing alcohol provides cooling to the reaction mixture and continuously strips by-products therefrom.

Start-up and shut-down of the process requires purging with an inert gas. For this purpose, carbon dioxide produced during a carbonate neutralization step according to the inventive process or other suitable strip gas is added to the vessel. The pressure in the reactor vessels 110–113 is controlled to maintain the desired temperature in the reaction mixture. An inert gas is also added via a conduit 140 which connects to the system 100 at a discharge of the condenser 128 to prevent an explosive mixture from forming in the vicinity of the condenser. Carbon dioxide from the carbonate neutralization, or another inert gas source, such as nitrogen, or even an oxygen deficient off-gas from the sulfonation reactor would be suitable for addition through the conduit 140.

The operation temperature of a continuous bleaching step according to the invention as shown in FIG. 3 ranges from between about 90° C. and about 110° C. with a temperature range of about 98° C. to about 105° C. being preferred. Refluxing allows for very efficient heat transfer, near isothermal operating conditions and thus higher operation temperatures than the loop bleaching process described with respect to FIG. 1.

As with the bleaching systems described with respect to FIGS. 1 and 2, in the system 100 shown in FIG. 3, all of the bleaching equipment which is wetted by the reaction mixture is made from a non-metallic material or low-iron corrosion resistant alloy. However, similar to the semi-batch process, the heat transfer for the exothermic bleaching reaction is provided in a condenser 128 and vent system which may be made from stainless steel.

An advantage of the semi-batch and continuous processes according to the invention as illustrated in FIGS. 2 and 3 is that by-product oxygen and ethers are continuously removed from the system, improving process safety.

Water may also be stripped from the bleaching mixture by not returning the condensed liquid stream to either the vessel 64 (FIG. 2) or the vessel 110 (FIG. 3 and replacing the condensed liquid stream with a like amount of anhydrous methanol. This may be desirable if 50 wt. % hydrogen peroxide is not available.

Residual peroxides including hydrogen peroxide and possible organic peroxides may be destroyed by reacting them with reducing agents such as sulfur dioxide or the salts or acids thereof. This destruction of the residual peroxides is preferably performed as soon as possible after the bleaching process, during or immediately after neutralization of the product.

Furthermore, if the product is dried or the solvents are stripped, care must be taken that trace levels of organic peroxides do not concentrate in any downstream purification processes. When distillation is used, a small stream of aqueous reducing agent is added near the top of the distillation tower to react with any accumulating peroxides. The low or non-volatile reducing agent thereafter descends through the tower, eliminating any possibility of accumulation of peroxides. The bottom product of the tower can be routinely tested for excess reducing agent.

Neutralization with a Metal Hydroxide

A neutralization step of a sulfonation process according to the invention may be performed by reacting sulfonic acid with a liquid metal hydroxide. Neutralization with a metal hydroxide, such as sodium hydroxide produces a "high active" (greater than 55 wt. % active sulfonate) sulfonated paste with low net di-salt formation (less than about 1 wt. %) during neutralization. The term "high active" is used in the art to refer to a high amount of the preferred surface active ingredient in the reaction mixture (i.e. in this instance, a high amount of the salt of the sulfonic acid).

Preferred operation conditions for neutralizing with a metal hydroxide (particularly preferred sodium hydroxide at a concentration of 48 wt. % or greater) according to the invention include performing the neutralization at a pH range of about 4 to about 9 (particularly preferred about 5.5), a neutralization temperature of about 40° C. to about 70° C. (particularly preferred about 50° C.) and an alcohol (particularly preferred methanol) content of the reaction mixture entering the neutralization system of about 20 wt. % to about 40 wt. % (particularly preferred about 30 wt. %).

Figure 4:
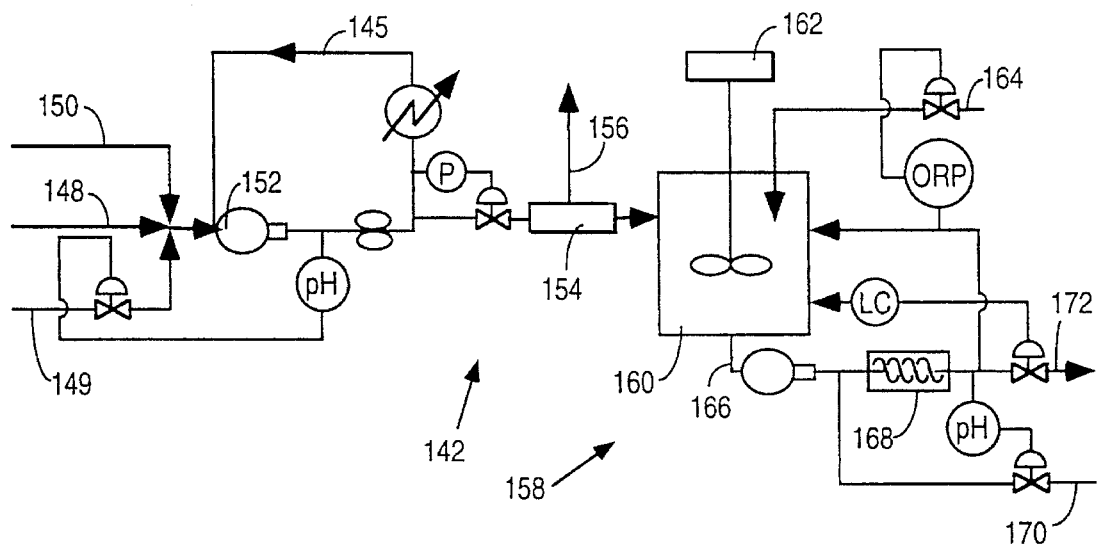
FIG. 4 is a process flow diagram illustrating a neutralization process step according to the invention for use with liquid bases followed by removal of gaseous by-products and destruction of residual peroxides.

A neutralization step of a sulfonation process according to the invention may be performed in a system generally designated 142 shown in FIG. 4. The sulfonic acid and liquid metal hydroxide enter a dominant bath recirculation loop 145 via conduits 148 and 149 respectively. An alcohol may also be added to the loop 145 through a conduit 150. The loop 145 is similar to the bleaching loop 34 shown in FIG. 1, but with the addition of a high shear mixer 152. Proper pH control and mixing are required because of the hydrolytic instability of the product in aqueous systems at low or especially high pH. From the loop 145 the neutralized product mixture is conveyed through a degasser 154 for removing off-gasses such as oxygen and ethers through a vent 156. Vent streams should be controlled to prevent an explosive atmosphere from forming. The neutralized product is then conveyed to process equipment utilized for the destruction of peroxides, generally designated 158. In a vessel 160 having a mixer 162, the product is mixed with a reducing agent, such as $SO_2$ or the salts or acids thereof (e.g. $SO_2$, $H_2SO_3$, $NaHSO_3$, and $Na_2SO_3$) from a conduit 164. The resulting product exits the vessel through a conduit 166 and may be pumped to a mixer 168 where the product is mixed with a base, such as 50% NaOH from a conduit 170 to control the product pH. The product is conveyed from the process equipment for storage or further processing through a conduit 172.

Neutralization with Metal Carbonate

A neutralization step of a sulfonation process according to the invention may be performed by reacting sulfonic acid with a solid metal carbonate. Neutralization with a metal carbonate, such as sodium carbonate also produces high active (greater than 60 wt. % active sulfonate) sulfonated paste with essentially no net di-salt formation (less than 1 wt. %) during neutralization. Preferred operation conditions for neutralizing with a metal carbonate according to the invention include performing the neutralization in the presence of at least 20 wt. % alcohol, preferably methanol to result in a neutralization process which does not require mechanical degassing.

Neutralizing with solid sodium carbonate (available as dense soda ash) is preferred because it is less expensive than other bases. When metal carbonates are utilized for the neutralization process, there is less water in the reaction mixture and lower peak pH values are produced. Also, the sodium carbonate advantageously produces less heat of neutralization than what is exhibited by metal hydroxides during neutralization.

During bleaching and neutralization of the reaction mixture, oxygen and ethers are formed. These gasses must be removed from the reaction system, either by mechanical degassing or by stripping. Neutralization with a metal carbonate advantageously provides an improvement in the safety of the overall sulfonation process. Carbon dioxide is formed during the neutralization in adequate amounts to strip oxygen from the reaction mixture. Because carbon dioxide is produced throughout the reactor, the oxygen stripping is very efficient. Furthermore, the carbon dioxide formed during the process provides nearly complete removal of dimethyl ether in an inert atmosphere. Because the boiling point of oxygen is lower than the boiling point of dimethyl ether (−23° C.), oxygen is stripped to a greater extent than dimethyl ether.

Figure 5:
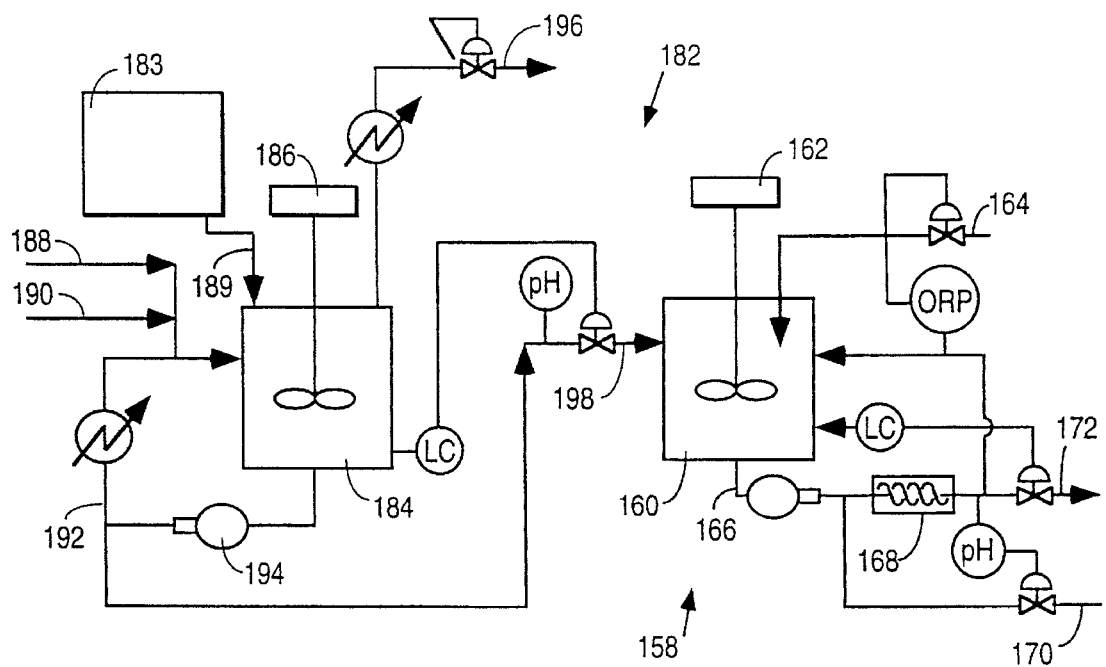
FIG. 5 is a process flow diagram illustrating a neutralization process step according to the invention for use with solid bases followed by the removal of gaseous by-products and destruction of residual peroxides.

A neutralization step of a sulfonation process according to the invention utilizing a metal carbonate may be performed in a system generally designated 182 shown in FIG. 5. The sulfonic acid and solid metal carbonate from a carbonate feeder 183 enter a vessel 184 having a mixer 186 via conduits 188 and 189 respectively. An alcohol may also be added to the vessel 184 through a conduit 190. The vessel 184 is preferably a continuous stirred tank reactor with continuous addition of acid and base. This method requires a reaction mixture of sufficiently low viscosity to allow the rapid disengagement of the evolved $CO_2$ and therefore requires greater than 20 wt. % alcohol, preferably methanol, in the fatty acid ester sulfonate paste entering the system 182.

Connected to the vessel 184 is a recycle loop 192 through which a reaction mixture may be circulated via a pump/grinder 194 to provide further mixing of the reactants. Carbon dioxide, oxygen, and other gasses may be removed from the vessel 184 through a vent 196. The neutralized product is then conveyed through a conduit 198 to the process equipment 158 described previously with reference to FIG. 4.

Figure 6:
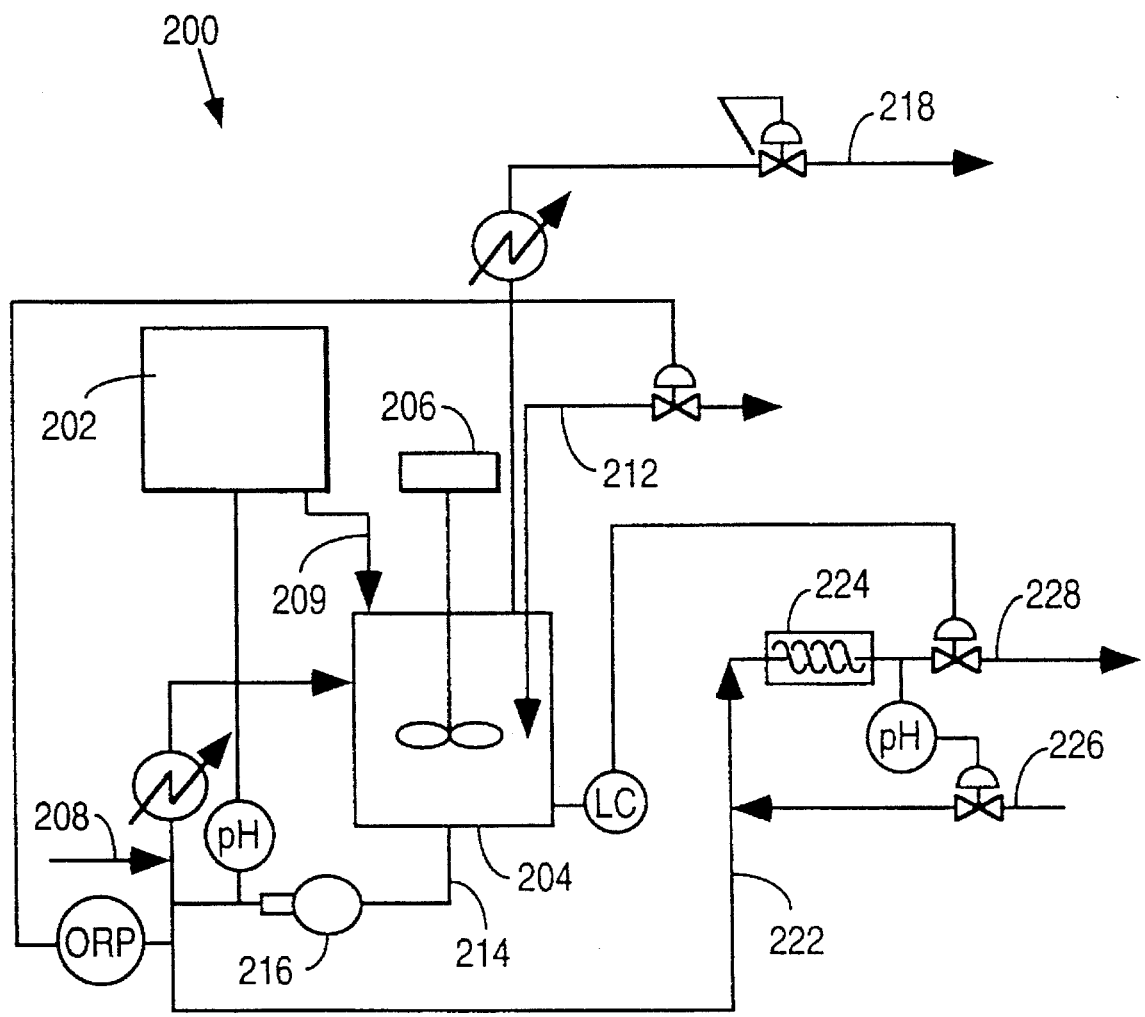
FIG. 6 is a process flow diagram illustrating a neutralization process step according to the invention for use with solid bases and combined with the removal of gaseous by-products and destruction of residual peroxides.

Carbonate neutralization and peroxide destruction may be performed in the same reaction vessel as illustrated in a system generally designated 200 in FIG. 6. By simply adding the reducing agent to the neutralization reactor, and controlling the oxidation reduction potential at the outlet, the second vessel 160 and pH control shown in FIG. 5 are eliminated.

In particular, the system 200 shown in FIG. 6 illustrates a neutralization step of a sulfonation process according to the invention utilizing a metal carbonate wherein sulfonic acid and solid metal carbonate from a carbonate feeder 202 enter a vessel 204 having a mixer 206 via conduits 208 and 209 respectively. The vessel 204 is preferably a continuous stirred tank reactor with continuous addition of acid and base. This method also requires a reaction mixture of sufficiently low viscosity to allow the rapid disengagement of the evolved $CO_2$ and therefore requires greater than 20 wt. % alcohol, preferably methanol, in the fatty acid ester sulfonate paste entering the system 200.

A reducing agent, such as $SO_2$ or its acids or salts is added to the vessel 204 via a conduit 212 and reacts with excess hydrogen peroxide in the system. Connected to the vessel 200 is a recycle loop 214 through which a reaction mixture may be circulated via a pump/grinder 216 to provide further mixing of the reactants. Carbon dioxide, oxygen, dimethyl ether, nitrogen, and other gasses may be removed from the vessel 184 through a vent 218.

Because a post pH adjustment step may be required at the discharge of the vessel 204, the product exiting the vessel through a conduit 222 may be pumped to a mixer 224 where the product is mixed with a base, such as 50% NaOH from a conduit 226. This pH control allows flexibility in operation so that bicarbonate levels in the product may be reduced. The pH adjusted product is conveyed from the process equipment for storage or further processing through a conduit 228.

The process equipment described above with respect to FIGS. 5 and 6 may be utilized for a neutralization process using other solid bases such as metal hydroxides and magnesium oxide with improved performance over aqueous systems. Furthermore a variety of organic acids may be neutralized in this way to produce a low water, highly active product.

The method of neutralization according to the inventive process utilizing a solid metal carbonate is especially suited where a final drying step to a solvent free form is desired. An alcohol solvent is more volatile, and less energy is required to remove the alcohol than water. Also, materials that are prone to hydrolysis are more stable when neutralized with a metal carbonate base. Materials that require drying but are very viscous in aqueous pastes are much easier to process with this neutralization method. The extremely viscous gel phases that form with water are thus avoided and the paste prior to and during drying has a much lower viscosity.

EXAMPLES

The invention is further described and illustrated by the following detailed examples which are not intended to be limiting.

Example 1

Preparation of Sodium Alpha Sulfo Methylester (SASME)-Neutralizing with NaOH Feedstocks The following feedstocks were utilized to prepare a neutralized fatty acid ester sulfonate according to the invention:

The fatty acid ester feedstock was a palm-stearin methylester manufactured by Henkel/Emery and sold under the designation ME-AS-16. The specifications and carbon distribution for the methylester are shown in Table 1.

TABLE 1

| Chain Length | Composition |
| --- | --- |
| C12 | 0 to 1% |
| C14 | 1 to 3% |
| C16 | 46 to 51% |
| C17 | 0 to 2% |
| C18 | 44 to 51% |
| Acid Value | <1.0 |
| Unsaponifiable | <1.0 |
| Saponification # | 197 to 200 |
| Average Molecular Weight | 281 |
| Iodine Value | <0.5 |

The $SO_3$ was produced by catalytically oxidizing $SO_2$ with a dry (Dew point of less than $-55°$ C.) air stream.

For bleaching, 50 wt. % technical grade hydrogen peroxide was utilized. Lower concentrations of hydrogen peroxide were made by diluting the 50 wt. % hydrogen peroxide with distilled water. Technical grade methanol (less than 500 ppm water) was added to the bleaching system.

For the neutralization portion of the process, the liquid base utilized was 50% technical grade NaOH or dry soda ash.

Process

With reference to FIG. 1, the sulfonation experiment was performed in a pilot plant comprising a falling film reactor 12 and a digester 16. The reactor 12 included a nominal 0.6 inch inside diameter jacketed tube which was 4.5 feet long and mounted in a vertical position. The liquid palm-stearin methylester feedstock (referred to as ME in the tables) from a conduit 18 was distributed to the inside wall of the tube reactor 12 and $SO_3$ and air from conduit 20 were introduced to the center of the tube. As the gas and liquid moved down the tube, $SO_3$ was absorbed and complexed or reacted. At the bottom of the reactor, a recycle stream of the reaction liquid was introduced at a 10:1 ratio to the liquid flowing down the tube. The recycle stream included the methylester (ME), methylester/sulfur trioxide complex (ME:$SO_3$), alpha sulfo methylester (ASME), and alpha sulfo methylester/sulfur trioxide complex (ASME:$SO_3$), along with sulfur dioxide, carboxylic acid, sulfuric acid, and hydrogen methyl sulfate. The gas and liquid then entered a cyclone 14 which disengaged the liquid and directed the gas through a vent 24 to a scrubber train. The liquid was then recirculated via a gear pump through a heat exchanger 26 to control the loop temperature to be the same as the desired digestion temperature.

Acid digestion was then performed in one of two jacketed plug flow reactors 16. The digestion temperature was adjusted as needed to provide adequate conversion of the methyl ester. The temperature in the digester 16 ranged from about $80°$ C. to about $95°$ C. and residence time for the crude acid in the digester 16 was about 30 minutes.

The crude acid was then transported through a conduit 28 to a bleaching apparatus 32 where it was treated with about 3 wt. % hydrogen peroxide (50%) and about 30 wt. % methanol, based upon the weight of the methyl ester and $SO_3$ feeds into the pilot plant.

The pilot plant bleaching apparatus utlized for the process included a non-metallic bleaching loop 34 and a plug flow digester 38. The bleaching loop was polymer coated (TEFLON®) steel pipe and included a centrifugal pump with a graphite plate (ALFA LAVAL) and frame heat exchanger. The methanol and $H_2O_2$ were metered into the loop 34 just before a polymer coated (TEFLON®) centrifugal pump (DURCO 1½×6), then into the heat exchanger 36 where the substantial heat of reaction was removed. The loop 34 was connected to one of two polymer coated (TEFLON®) plug flow reactors 38 with internal polymer coated (TEFLON® PFA) cooling coils where the reaction was completed. Residence time of the reaction mixture in the bleaching digester was controlled by varying the feed rate of organic and air/$SO_3$ in the process. The temperature in the loop and digester was maintained at approximately 99° C.

The resulting ASME was then transported through conduit 44 for neutralization which was performed continuously in a reactor loop 46. The ASME and 50% NaOH were introduced into separate channels of an annular feed tube into a recirculating stream of neutralized methyl ester sulfonate. The loop 46 was recirculated with a positive displacement in a progressive cavity pump (Lederle SFPL 1N). The loop temperature was controlled by adjusting the water temperature in the jacketed pipe of the neutralizer loop. The pH was controlled by a feedback controller that adjusted the 50% sodium hydroxide feed rate.

The process stream compositions, operating conditions and times for the experiment are set forth in Tables 2 and 3 below:

TABLE 2

Mass Balance w/NaOH Neutralization for: Palm-Stearin MES 3% $H_2O_2$ & 30% MeOH

| Component | MW | Feed Gas (20)[1] | Feed Organic (18) | Outlet Reactor (22) | Vent (24) | Outlet Recycle (27) | Outlet Digester (28) | Feed Alcohol (40) | Feed $H_2O$[2] (30) | Outlet Recycle (42) | Outlet Bleacher (44) |
|---|---|---|---|---|---|---|---|---|---|---|---|
| Air-$O_2$ | 28 | 29.8 | | 0.0 | 29.8 | | 0.0 | | | | |
| $SO_3$ | 80.1 | 6.4 | | 0.0 | 0.00 | 0.00 | 0.00 | | | 0.0 | 0.0 |
| $SO_2$ | 84.1 | 0.1 | | 0.5 | 0.30 | 0.2 | 0.3 | | | 0.0 | 0.0 |
| Methylester or Oils | 279 | | 18.0 | 3.0 | 0.01 | 3.0 | 1.2 | | | 1.2 | 1.0 |
| ME:$SO_3$ Complex | 359 | | | 4.0 | 0.01 | 4.0 | 0.0 | | | 0.0 | 0.0 |
| ASME:$SO_3$ Complex | 439 | | | 6.7 | 0.02 | 5.6 | 2.4 | | | 0.0 | 0.0 |
| Alpha Sulfo Methyl Ester (ASME) | 359 | | | 9.8 | 0.03 | 9.8 | 18.8 | | | 19.6 | 21.2 |
| Alpha Sulfo Carboxylic Acid (ASCA) | 345 | | | | | | 0.7 | | | 1.8 | 0.6 |
| Carboxylic Acid | 265 | | 0.04 | 0.04 | 0.00 | 0.04 | 0.04 | | | 0.04 | 0.04 |
| $H_2SO_4$ + Hydrogen Methyl Sulfate | | | | 0.6 | 0.00 | 0.5 | 0.7 | | | 1.7 | 1.7 |
| Methanol | 32 | | | | | | | 7.2 | | 7.1 | 6.8 |
| NaOH | 40 | | | | | | | | | | |
| NaASME (MES) | 381 | | | | | | | | | | |
| SASC (Di-Salt) | 389 | | | | | | | | | | |
| Sodium Carboxylate (Soap) | 287 | | | | | | | | | | |
| $Na_2SO_4$ + $NaSO_3OCH_3$ | | | | | | | | | | | |
| $H_2O_2$ | 34 | | | | | | | | 0.7 | 0.5 | 0.2 |
| $H_2O$ | 18 | | | | | | | 0.01 | 0.7 | 0.7 | 0.9 |
| Other | | 0.0 | 0.0 | 0.0 | 0.0 | 0.0 | 0.0 | 0.0 | 0.0 | 0.1 | 0.3 |
| TOTAL (kg/hr) | | 36.3 | 18.0 | 24.6 | 30.2 | 24.2 | 24.1 | 7.2 | 1.4 | 32.8 | 32.9 |
| Temp (°C.) | | 40 | 40 | 75 | 75 | 85 | 85 | 25 | 25 | 75 | 99 |
| Press psig | | | | 3 | 3 | 115 | 105 | | | 100 | 95 |
| Residence Time | | | | | | <5 min | 30 | | | <5 min | 60 |
| Klett (5% AM) | | | | 2000 | | 3000 | 11000 | | | 2500 | 150 |
| % ASME as Color Body | | | | 0.04 | | | 0.05 | | | 0.04 | 0.01 |
| Mol (MeOH/$H_2O$) | | | | | | | | | 5.6218 | 5.87 | 4.14 |

| Component | Feed NaOH (50) | Feed Solvent (52) | Outlet Nuet (54) | Wt % Paste (54) | Wt % AB Paste (54) |
|---|---|---|---|---|---|
| Air-$O_2$ | | | | 0.0% | 0.0% |
| $SO_3$ | | | | 0.0% | 0.0% |
| $SO_2$ | | | | 0.0% | 0.0% |
| Methylester or Oils | 0.0 | 0.0 | 0.7 | 1.6% | 2.8% |
| ME:$SO_3$ Complex | | | | 0.0% | 0.0% |
| ASME:$SO_3$ Complex | | | 0.0 | 0.0% | 0.0% |
| Alpha Sulfo Methyl Ester (ASME) | 0.0 | 0.0 | 0.0 | 0.0% | 0.0% |
| Alpha Sulfo Carboxylic Acid (ASCA) | | | | 0.0% | 0.0% |
| Carboxylic Acid | | | 0.00 | 0.0% | 0.0% |
| $H_2SO_4$ + Hydrogen Methyl Sulfate | 0.0 | 0.0 | 0.0 | 0.0% | 0.0% |
| Methanol | | | 6.8 | 16.7% | 28.7% |
| NaOH | 3.7 | | 0.0 | 0.0% | 0.0% |
| NaASME (MES) | | | 22.2 | 54.2% | 94.4% |
| SASC (Di-Salt) | | | 1.3 | 3.3% | 5.6% |
| Sodium Carboxylate (Soap) | | | 0.04 | 0.1% | 0.2% |
| $Na_2SO_4$ + $NaSO_3OCH_3$ | | | 2.3 | 5.7% | 9.8% |
| $H_2O_2$ | | | 0.05 | 0.1% | 0.2% |

TABLE 2-continued

Mass Balance w/NaOH Neutralization for: Palm-Stearin MES 3% $H_2O_2$ & 30% MeOH

| | | | | | |
|---|---|---|---|---|---|
| $H_2O$ | 3.7 | 0.6 | 6.9 | 16.9% | 29.1% |
| Other | 0.0 | 0.0 | 0.4 | 0.9% | 1.5% |
| TOTAL (kg/hr) | 7.4 | 0.6 | 41.0 | 100% | |
| Temp (°C.) | 25 | 25 | 60 | | |
| Press psig | | | 40 | | |
| Residence Time | | | | | |
| Klett (5% AM) | | | 100 | | |
| % ASME as Color Body | | | 0.005 | | |
| Mol (MeOH/$H_2O$) | | | 0.55 | | |

[1]Number in parenthesis with respect to each process stream is with reference to FIG. 1.

TABLE 3

Palm-Stearin MES
3% $H_2O_2$ & 30% MeOH

| | |
|---|---|
| $SO_3$ Mole ratio | 1.25 |
| $SO_3$ Conc. % | 7 wt. % |
| Alcohol Addition | 30.0 wt. % Based on Digested Acid |
| % $H_2O_2$ | 50 wt. % |
| $H_2O_2$ Addition | 3.0% Based on Digested Acid |

The colorimeter utilized to measure sulfonate color in the example was a Klett-Summerson Colorimeter utilizing a number 42 blue filter. The Klett colorimeter is commonly used for determination of sulfonate color. The method utilized to measure the sulfonate color was substantially similar to ASTM D 3673–87, Section 32. However, because the details of the testing differ somewhat, the method utilized is described below:

Bleached methyl ester sulfonate solutions are yellow hued and strongly absorb the blue light as compared to other sulfonates. Fatty methyl ester sulfonates and sulfonic acids from C10 to C22, bleached and unbleached, can be analyzed by this method.

Equipment:

Klett-Summerson Colorimeter

Blue Filter #42

40×20 mm cell 100 ml glass stoppered graduated cylinder

Reagents:

Isopropanol (reagent grade)

Dilute isopropanol:
  Mix: 1 liter isopropanol (reagent grade) with 1 liter water (distilled or deionized).

Procedure for Acid Samples:

1. For unbleached samples, weigh 0.1 g into a 100 ml stoppered graduated cylinder. For bleached samples, weigh 0.4 to 1.0 g of sample.

2. Fill with isopropanol to 100 ml. Warm and shake as needed to dissolve.

3. Using the 40 mm path, zero the colorimeter with the solvent used. Rinse the Klett cell with the sample, fill and read the sample.

Procedure for Neutral Samples:

1. For bleached samples, weigh 5.0 g of samples into a 100 ml stoppered graduated cylinder.

2. Fill with dilute isopropanol to 100 ml. Warm and shake as needed to dissolve.

3. Using the 40 mm path, zero the colorimeter with the solvent used. Rinse the Klett cell with the sample, fill and read the sample.

Calculations:

5% Klett (Active Basis) =

$$\frac{(\text{Klett reading}) * (500)}{(\% \text{ active by Hyamine Titration}) * (\text{g sample})}$$

As shown in Table 2, the final product had a color of less than 100 Klett on a 5% sulfonate basis.

Other results of the experiment are summarized in Table 4 below:

TABLE 4

| | |
|---|---|
| Yield from ME | 91% to MES only |
| Yield from ME | 96% to MES + Di-Salt |
| Percent Solids | 63% in Neutral Paste |

Example 2

Preparation of SASME-Neutralization Comparisons

The SASME for this example was made with the same feedstocks as described with respect to Example 1. With the exception of the neutralizing step and unless otherwise stated below, the SASME also was made according to the same process and with the same equipment and process parameters as described with respect to Example 1.

Two laboratory runs of pilot plant bleached ASME were performed to evaluate neutralization with sodium carbonate. For each run, ASME from the bleaching plug flow digester was batch neutralized in a 1-liter vacuum jacketed reactor having a glass stir paddle. A circulation jacket with inlet and outlet nozzles was located between the vacuum jacket and an interior reactor wall. The circulating jacket fluid was a 50/50 mixture of ethylene glycol and water. For purposes of comparison, a sample of acid prepared in each of the two runs was neutralized with liquid NaOH according to the process described in Example 1.

In both laboratory runs, the ASME was added to a sodium carbonate slurry. The ASME from the first run was made with a 24 wt. % addition of methanol, while the ASME from the second run was made with a 34 wt. % addition of methanol. The change in methanol addition changed the characteristics of the acid in that the first acid had to be heated to 60° C. to pump it into the reactor while the second acid was a liquid at room temperature.

For the first neutralization run, a slurry of 43.8 g. of $Na_2CO_3$ and 131.4 g. methanol was agitated in the reactor at 450 to 550 rpm with an anchor stirrer. Thereafter, 400 g. of bleached acid was added to the carbonate slurry over a period of 20 minutes. The reactor jacket was set to 43° C. and the peak reactor temperature was 46° C. The reactor was heated to 60° C. for 20 minutes after the addition was complete. The final mixture was acidic, and additional sodium carbonate was added to raise the pH.

For the second neutralization run, a slurry of 36.5 g. of $Na_2CO_3$ and 336 g. of neutral material from the first neutralization was added to the reactor. Thereafter, 283 g. of bleached acid was added to the carbonate slurry over a period of 15 minutes. The reactor mixing, temperature and exotherm were substantially the same as for the first neutralization run.

Table 5 shows an analytical summary of the two runs neutralized with sodium carbonate and with sodium hydroxide.

TABLE 5

| Yields* | Run 1-MeOH Slurry | | Run 2-MES Slurry | |
| --- | --- | --- | --- | --- |
| | w/$Na_2CO_3$ | w/NaOH | w/$Na_2CO_3$ | w/NaOH |
| Di-Acid in Feed | 4.0% | 4.0% | 4.8% | 4.8% |
| Oil in Feed | 7.8% | 7.8% | 4.2% | 4.2% |
| Di-Salt in Neutral Product | 4.5% | 4.8% | 4.5% | 6.0% |
| Net Di-Salt | 0.5% | 0.8% | −0.3% | 1.2% |
| Oil in Neutral Product | 4.0% | 4.3% | 3.4% | 2.9% |
| Percent Actives | 63.9% | 64.7% | 64.3% | 59.0% |
| Density (g/ml) | 0.89 | 0.15 | 0.90 | 0.18 |

*All percentages are weight percent.

In both runs, the sodium carbonate neutralized product had a very low viscosity as compared to the sodium hydroxide neutralized samples. The density values indicate the level of degassing that occurred during the neutralization. The density measurements for the NaOH neutralization are at atmospheric pressure at the discharge of the pilot plant neutralizer.

Carbon dioxide disengagement occurred easily in the reactor utilizing sodium carbonate with very little frothing on the surface of the reactor. The amount of carbon dioxide produced during the neutralization was approximately equal to half the moles of sulfur trioxide originally added. Because carbon dioxide is produced throughout the neutralization reactor, very efficient stripping of the oxygen formed during the bleaching step is believed to have occurred.

Dimethyl ether was also stripped in the batch reactor. Analysis showed that approximately 99% of the dimethyl ether formed during each run was removed during batch carbonate neutralization.

Color of less than 100 Klett on a 5% sulfonate basis was observed for neutral product from each of the runs neutralized with sodium carbonate.

Example 3

Bleaching Experiments

Initial work with bleaching methylester sulfonic acid was conducted in passivated 316 stainless steel equipment. This work showed that heating the bleaching system above 75° C. resulted in darker colors than at lower temperatures. Operation at the higher temperature resulted in a rapid exotherm and the total consumption of hydrogen peroxide. Once all the hydrogen peroxide was consumed, the color of the acid increased with time.

Figure 7:
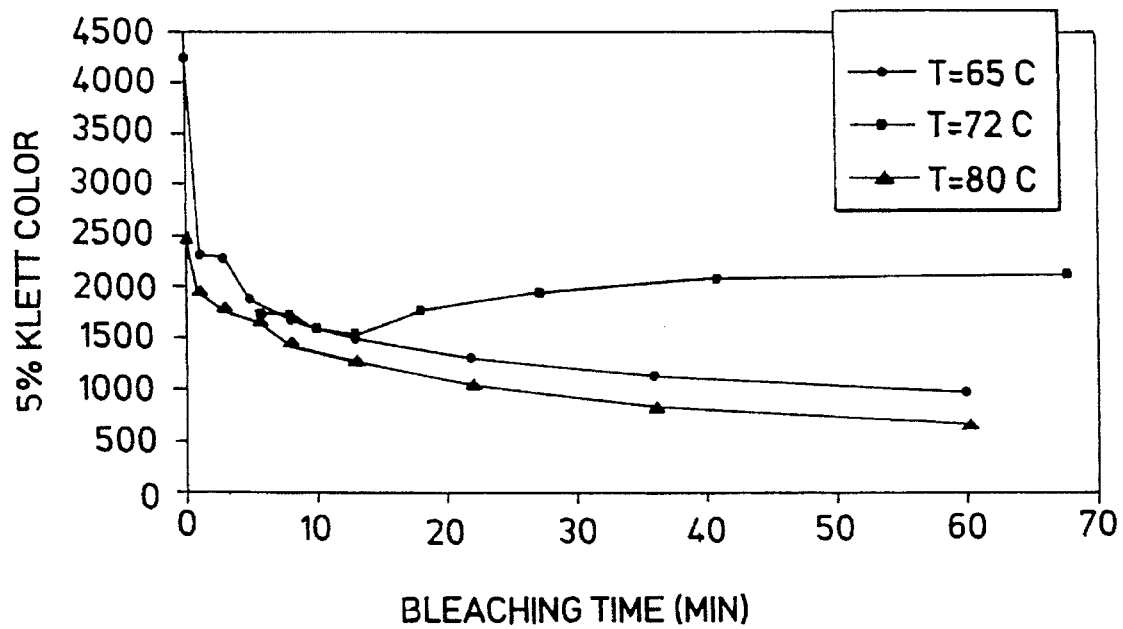
FIG. 7 is a graph depicting color (5% Klett) of bleached methylester sulfonic acid vs. bleaching time (min.) in a stainless steel reactor at bleaching process temperatures of 65° C., 72° C. and 80° C. in Example 3.

To illustrate, FIG. 7 compares runs at 65° C., 72° C. and 80° C. The material for these runs was a tallow methylester sulfonated in a falling film reactor described in Example 1 at a methylester to $SO_3$ mole ratio of 1:1.5. The acid was digested for 10 minutes at 90° C., and then 2 wt. % active 35% hydrogen peroxide was added along with 10% methanol into a bleaching loop at 72° C. Material from the bleaching loop was then batch digested in a 316 stainless steel Paar bomb reactor. The color of the acid fell more quickly at 72° C. than at 65° C. However, the color at 80° C. fell for about 10 minutes, then started to increase. Temperature in these runs was controlled at plus or minus 2° C.

Apparently, the surface passivation in the stainless steel was being attacked by the slightly hydrated acid mixture which created a surface capable of catalyzing hydrogen peroxide decomposition.

Figure 8:
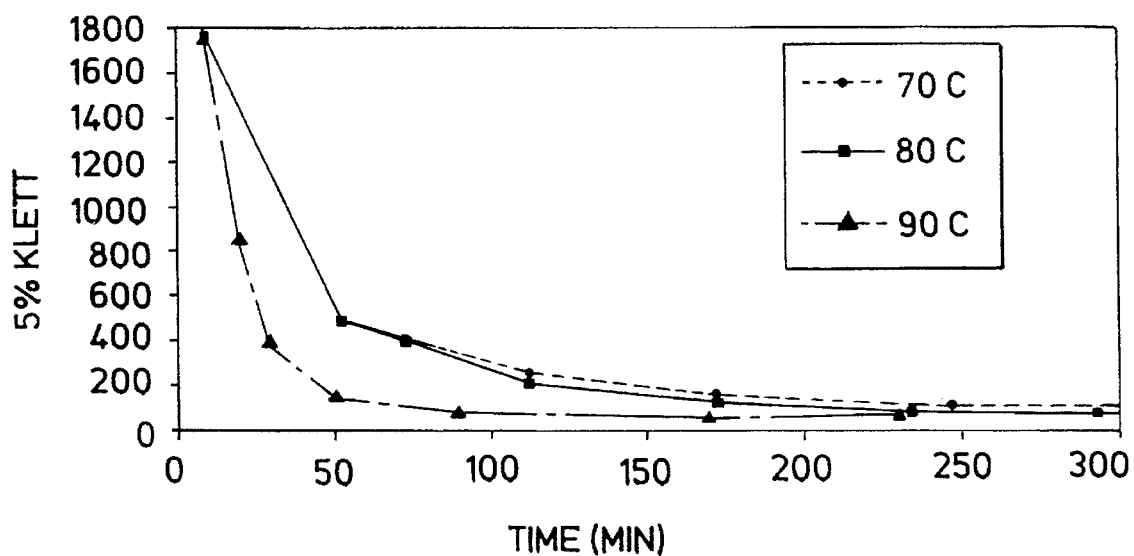
FIG. 8 is a graph depicting color (5% Klett) of bleached methylester sulfonic acid vs. bleaching time (min.) in a glass reactor at bleaching process temperatures of 70° C., 80° C. and 90° C. in Example 3.

For comparison, FIG. 8 shows batch bleaching results in glass at 70° C., 80° C. and 90° C. The material for these runs was a palm stearin methylester sulfonated in a falling film reactor described in Example 1 at a methylester to $SO_3$ mole ratio of 1:1.3. The acid was digested for 27 minutes at 85° C., and then 4 wt. % of active 50% hydrogen peroxide was added along with 20 wt. % methanol into a bleaching loop at 70° C. Material from the bleaching loop was then batch digested in a 500 ml 3 neck flask in a temperature controlled water bath. The color of the acid fell slightly more quickly at 80° C. than at 70° C. However, the color at 90° C. fell much more quickly than at the lower temperatures. Temperature in these runs was also controlled at plus or minus 2° C.

Figure 9:
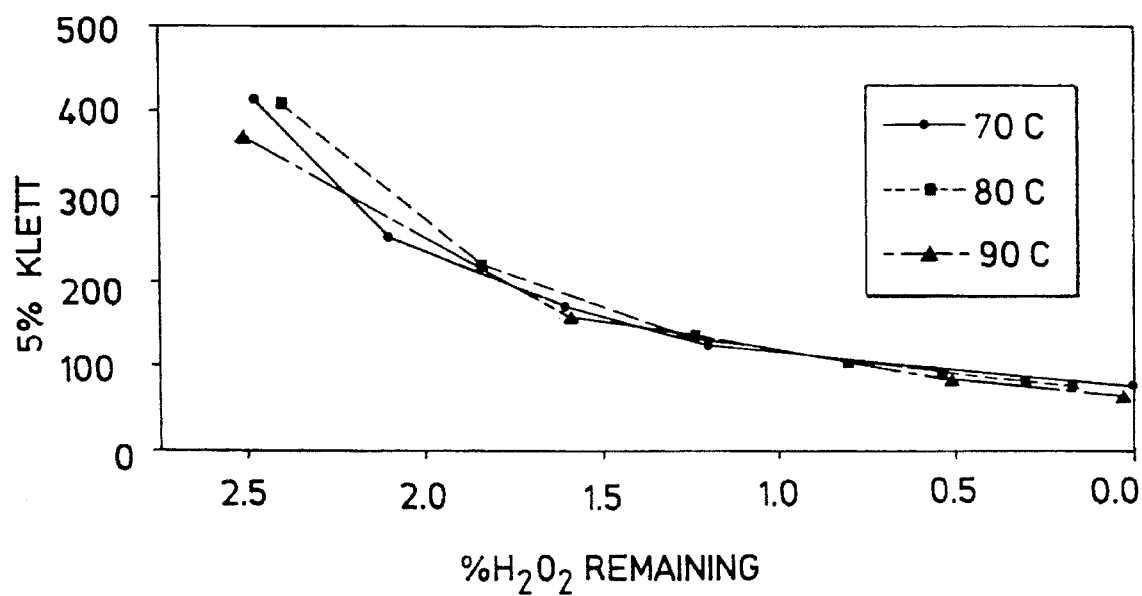
FIG. 9 is a graph depicting color (5% Klett) of bleached methylester sulfonic acid vs. percentage of hydrogen peroxide remaining in the reaction mixture in a glass reactor at bleaching process temperatures of 70° C., 80° C. and 90° C. in Example 3.

FIG. 9 shows the color of the bleached acid vs. the remaining peroxide percentage for the same three runs shown in FIG. 8. The three curves show the same relationship between hydrogen peroxide consumption and reduction in color, indicating that no additional decomposition of hydrogen peroxide is occurring.

Example 4

Bleaching Experiments: MeOH Addition

To determine the effect of methanol addition on bleaching and neutralization, four laboratory runs were performed to prepare SASME made with the same feedstocks, process equipment and parameters as described with respect to Example 1. The process described with respect to Example 1 was also followed for each run with the exception that varying methanol amounts were added during the bleaching step of the process. The bleach digestion temperature for each run was 100° C. and the bleach digestion time was 60 minutes. Hydrogen peroxide (50 wt. % concentration) addition was about 3 wt. % based upon the acid.

A sample of a bleached product from each run was neutralized in the laboratory in methanol with sodium carbonate. The results of these runs and yield to di-salt comparison with the continuous pilot plant sodium hydroxide neutralization results for each run are set forth in Table 6. The standard deviation results are from four sets of replicates, with a total of five degrees of freedom.

TABLE 6

| | | | | | |
| --- | --- | --- | --- | --- | --- |
| Methanol Addition (% of Acid) | 10 | 20 | 30 | 40 | Std. Dev. |
| Klett Color of Neutral MES | 106 | 80 | 86 | 95 | 10 |
| % Yield to Di-Salt (Carbonate) | 9.8 | 6.1 | 4.1 | 3.8 | 0.7 |
| % Yield to Di-Salt (MES neutralized with 50% NaOH) | 14.8 | 8.5 | 5.5 | 4.9 | 1.6 |

It is apparent from Table 6 that the di-salt yield decreases dramatically when methanol addition is increased.

Example 5

Extractable Oils Experiment

A series of experiments were run that examined the effect of mole ratio, digestion temperature and digestion time on the responses color and petroleum ether extractable oils (PEE) for a typical palm derived palm-stearin methyl ester (Henkel ME-AS-16). The sulfonations were carried out in the falling film reactor described in Example 1 and the digestions were carried out in batch with a Paar stirred reactor. All combinations of mole ratios of methyl ester to $SO_3$ of 1:1.1, 1.3 and 1.5 and digest temperatures of 70° C., 80° C. and 90° C. were run, each with 11 samples at digest times from 2 minutes to 124 minutes.

Figure 10:
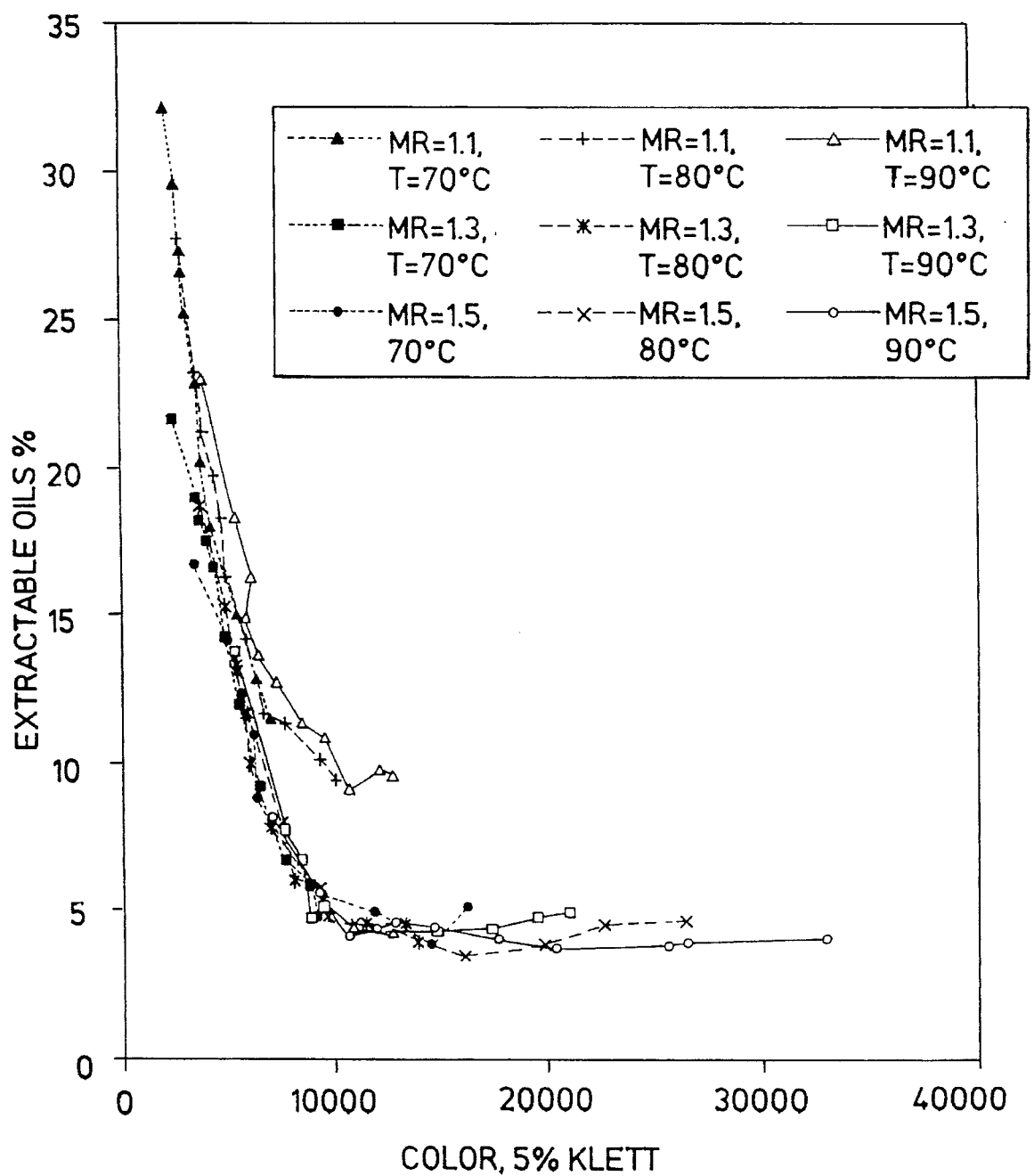
FIG. 10 is a graph depicting percentage of extractable oil in methylester sulfonic acid vs. color (5% Klett) of the acid processed at various temperatures and with various sulfur trioxide to methyl ester feedstock mole ratios in Example 5.

The results of the experiments are shown in FIG. 10 which illustrates that over a broad range of mole ratio, digestion temperature and digestion time, the same product quality can be achieved. For the material tested, a mole ratio of 1.1 is below the critical level and so there is a lower level of conversion (higher oils) for the same color compared to higher mole ratios. For the two higher mole ratios, essentially the same relationship between extractable oils and color was achieved for all combinations of digestion temperature and digestion time.

Example 6

Change in Oils Through a Process

Table 7 shows the analytical results for the sulfonation, bleaching and neutralization for the same palm-stearin methylester feedstock used in Example 5. This feedstock was sulfonated at a methylester to $SO_3$ mole ratio of 1:1.25 in the pilot plant described in Example 1. Bleaching was achieved with a 2.5 wt. % active addition of 50% hydrogen peroxide and a 20 wt. % co-addition of methanol. Neutralization was with 50% sodium hydroxide. The process was performed as described in Example 1.

TABLE 7

| Process Sample | Yield From Methylester (in wt. %) | | | |
|---|---|---|---|---|
| | Non-volatile Oils | Volatile Oils | Di-Salt* | MES** |
| Acid Digester | 6 | 0 | 18 | 75 |
| Bleaching Loop | 5 | 1 | 5 | 88 |
| Bleach Digester | 2 | 3 | 4 | 92 |
| Neutralizer | 1 | 2 | 6 | 91 |

*Intermediate (III) or Di-Salt (V)
**Methylester Sulfonic Acid or Methylester Sulfonate This experiment shows that selecting the severity of sulfonation based on the extractable oil in the digested methylester sulfonic acid can lead to unnecessarily high colors and potentially lower yield. Even when there is a substantial amount of extractable oils in the digested acid, 5% or more, there is very little volatile oils, indicating essentially no unreacted methylester. Any effort to reduce volatile oils further would significantly increase color and other sulfonation byproducts without benefit, since essentially all the methylester feed stock has reacted. Further, some of the extractable oils are converted to sulfonates, possibly by the hydrolysis of sultones during bleaching and especially neutralization. By examining the yields in Table 7, this behavior can be readily seen. This means that much higher levels of extractable oils are acceptable in the digested sulfonic acid than are desired in the neutral paste. It has been found that in most cases, about 50% of the non-volatile oils are converted to a water soluble form through the process.

Example 7

Neutralization With Metal Hydroxides

To determine the effect of the factors of neutralizer temperature, neutralizer pH and total methanol addition for ASME neutralized with NaOH, a statistical experimental design was run on the process described in Example 1 with the factors listed in Table 8 being held constant.

TABLE 8

| Factors Held Constant | Value |
|---|---|
| Feed | Henkel ME-AS-16 |
| Percent $SO_3$ in Air | 4% |
| Total ME + $SO_3$ (lb/hr) | 20.0 |
| Mole Ratio $SO_3$:ME | 1.25 |
| $H_2O_2$ Concentration (% in water) | 50.% |
| $H_2O_2$ Addition (% ME + $SO_3$) | 3.6% |
| Methanol Addition to Bleacher (% of ME + $SO_3$) | 20.0% |

Table 9 sets forth the factors and ranges studied.

TABLE 9

| Factors | Low | Mid | High |
|---|---|---|---|
| Neutralizer Temperature (°C.) | 40 | 55 | 70 |
| Neutralizer pH | 5 | 7 | 9 |
| Total Methanol Addition (% of acid) | 20% | 60% | 99% |

Numerous runs were performed, during which a variety of analytical and physical data were gathered. The responses were analyzed and a model prediction for the optimum operating conditions is shown in Table 10.

TABLE 10

| Factors | Optimum Point |
|---|---|
| Neutralizer Temperature (°C.) | 50 |
| Neutralizer pH | 6.0 |
| Total Methanol Addition (% of SA) | 30% |

Figure 11:
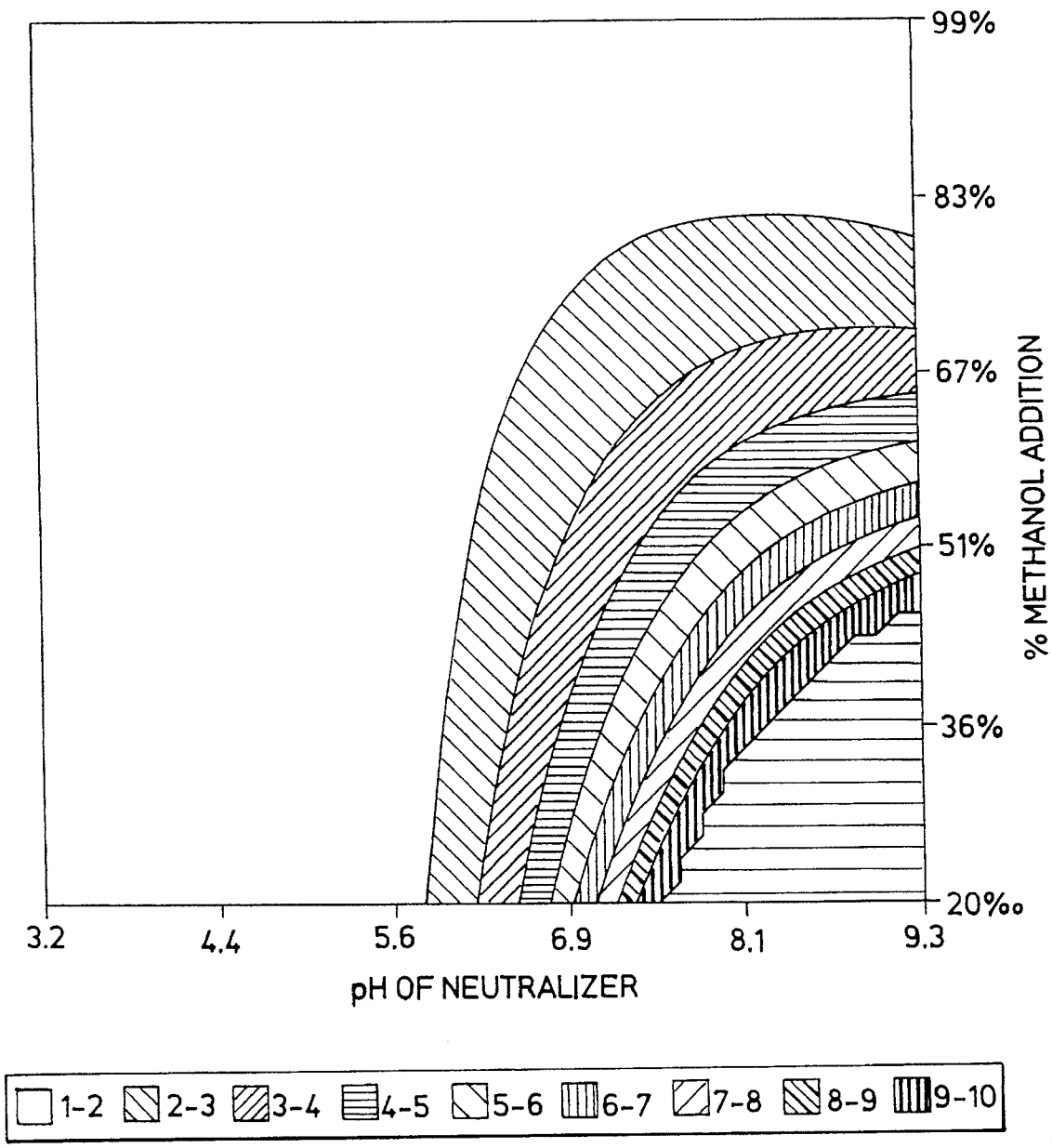
FIG. 11 is a contour plot depicting a model response based on the experiments of Example 7 depicting net di-salt formation in sodium hydroxide neutralization at 50° C. as a function of pH and percent methanol addition.
Figure 12:
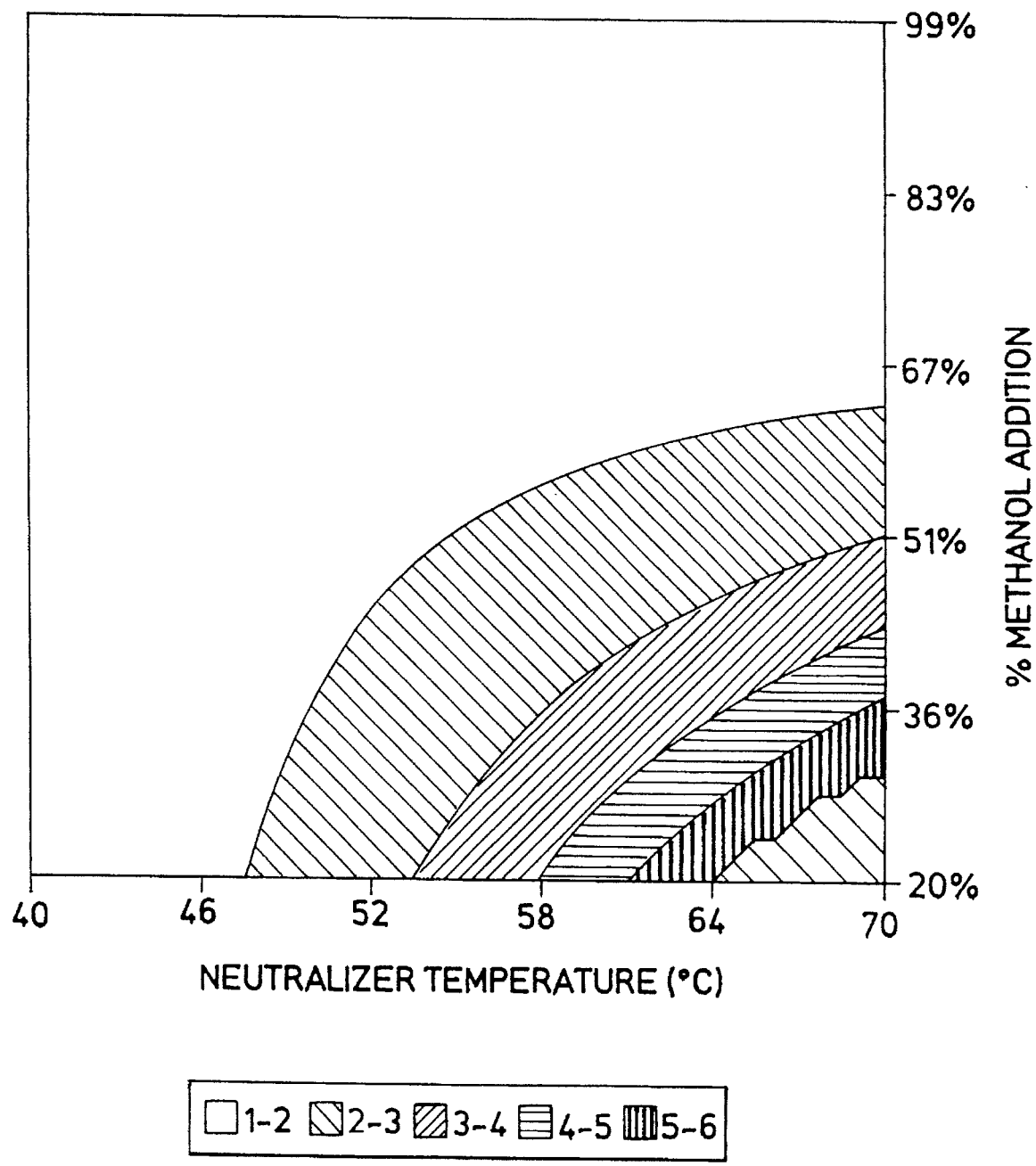
FIG. 12 is a contour plot depicting a model response based on the experiments of Example 7 depicting net di-salt formation in sodium hydroxide neutralization at a pH of 6 as a function of temperature and percent methanol addition.
Figure 13:
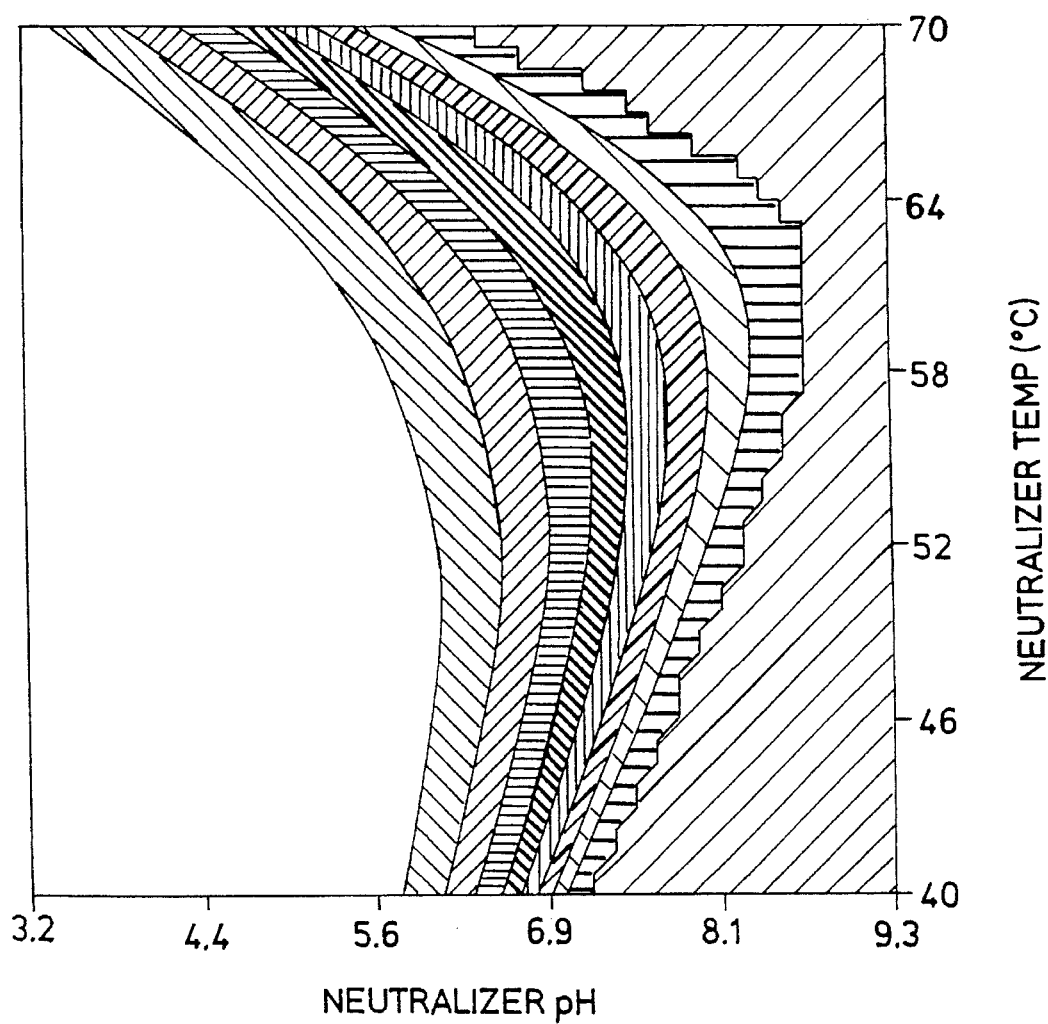
FIG. 13 is a contour plot depicting a model response based on the experiments of Example 7 depicting net di-salt formation in sodium hydroxide neutralization at 30% methanol addition as a function of neutralizer pH and neutralizer temperature.

The model responses of the experiment are also set forth in FIGS. 11–13. These figures are contour plots which show net di-salt yields as contour lines that depend on the value of the two factors on the x and y axes, much like a topographical map shows elevation for different longitude and latitude values. The response model for the experimental designs used in the studies is quadratic and understanding the size and shape of the region characterized by the designed experiment is critical to avoid using the model created with the design outside of the range of experimental data. Since the model is not designed to intrinsically describe the mechanical or chemical behavior of the system, the predictions of the model outside the range of data to which it was fitted is not related in any way to the potential behavior of the system. The areas outside of the range of data should therefore be ignored.

FIG. 11 shows the net yield to di-salt percentage for neutralization with sodium hydroxide as a function of pH and methanol addition (percent of acid). FIG. 12 shows the effect of neutralizer temperature (° C.) and methanol addition (percent of acid) on di-salt yield percentage. FIG. 13 shows the effect of neutralizer pH and neutralizer temperature (° C.) on di-salt yield percentage. The data shows a decrease in net yield to di-salt with increasing methanol addition. The effect is most pronounced at pH values above 6.0 and temperatures above 50° C.

The foregoing detailed description is given for clearness of understanding only, and no unnecessary limitations are to be understood therefrom, as modifications within the scope of the invention will be apparent to those skilled in the art.

I claim:

1. In a process for preparing a sulfonated fatty acid ester surfactant including the steps of
   (a) sulfonating a fatty acid ester thereby producing a crude sulfonic acid;
   (b) reacting the crude sulfonic acid with a bleaching agent and an alcohol; and
   (c) neutralizing the product formed in step (b);
   the improvement comprising the following expedients:
   (i) providing process equipment for performing step (b) comprising at least one of a continuous reactor vessel, a recirculation loop, a plug flow reactor, and a pressurized batch reactor vessel, said process equipment made from materials selected from the group consisting of non-metallic materials and low-iron, corrosion resistant alloys, said process equipment being wetted by the sulfonic acid and the bleaching agent during step (b); and
   (ii) performing the neutralizing step (c) with a solid base in the presence of solvent in an amount sufficient to form a neutralization mixture in the form of one of a solution and a slurry, said solvent being predominantly alcohol.

2. The improvement according to claim 1 wherein the fatty acid ester is sulfonated with $SO_3$ and the ester to $SO_3$ mole ratio in step (a) ranges between about 1:1.1 to about 1:1.5.

3. The improvement according to claim 1 wherein step (a) further comprises digesting the reactants at a temperature range of between about 80° C. and about 95° C.

4. The improvement according to claim 3 wherein the time and temperature of digesting is controlled to result in a crude sulfonic acid having about 4 wt. % to about 6 wt. % petroleum ether extractable oils.

5. The improvement according to claim 1 comprising performing step (b) at a temperature of at least 91° C. in process equipment selected from the group consisting of non-metallic materials and low-iron, corrosion resistant alloys.

6. The improvement according to claim 5 wherein step (b) is performed at a temperature range of between about 91° C. and about 110° C.

7. The improvement according to claim 5 wherein step (b) is performed at a temperature range of between about 95° C. and about 105° C.

8. The improvement according to claim 1 wherein the bleaching agent is hydrogen peroxide.

9. The improvement according to claim 1 wherein the bleaching step (b) further comprises continuously refluxing the alcohol during bleaching and stripping gaseous by-products from the product formed during step (b) with said alcohol.

10. The improvement according to claim 9 including stripping water from the product formed during step (b) and replacing said water with an approximately equal amount of alcohol.

11. The improvement according to claim 1 wherein the alcohol is selected from the group consisting of primary alcohols having 1 to 4 carbon atoms, secondary alcohols having 3 to 4 carbon atoms, and mixtures thereof.

12. The improvement according to claim 11 wherein the alcohol is methanol.

13. The improvement according to claim 1 wherein the alcohol addition ranges between about 21 wt. % and about 40 wt. % based upon the crude sulfonic acid weight.

14. The improvement according to claim 1 further comprising continuously stripping oxygen and ethers after the bleaching step (b).

15. The improvement according to claim 1 comprising expedient (i) and in the absence of expedient (ii) wherein a liquid base is utilized for the neutralizing step (c).

16. The improvement according to claim 15 wherein the alcohol addition ranges between about 21 wt. % and about 40 wt. % based upon the crude sulfonic acid weight.

17. The improvement according to claim 15 wherein the liquid base is a sodium hydroxide solution.

18. The improvement according to claim 1 wherein a solid metal carbonate is utilized for the neutralizing step (c).

19. The improvement according to claim 18 wherein the alcohol addition ranges between about 21 wt. % and about 40 wt. % based upon the crude sulfonic acid weight.

20. The improvement according to claim 18 wherein the solid metal carbonate is sodium carbonate.

21. The improvement according to claim 1 further comprising reacting residual bleaching agents and organic peroxides from the product formed in step (b) with a reducing agent.

22. The improvement according to claim 21 wherein the reducing agent is selected from the group consisting of $SO_2$, salts of $SO_2$, acids of $SO_2$, and mixtures thereof.

23. The improvement according to claim 18 further comprising reacting residual bleaching agents and organic peroxides from the product formed in step (b) with a reducing agent during step (c).

24. A process for preparing a sulfonated fatty acid ester surfactant comprising:
   (a) sulfonating a fatty acid ester thereby producing a crude sulfonic acid;
   (b) reacting the crude sulfonic acid with a bleaching agent and an alcohol in process equipment comprising at least one of a continuous reactor vessel, a recirculation loop, a plug flow reactor, and a pressurized batch reactor vessel, said process equipment wetted by the sulfonic acid and the bleaching agent being made from materials selected from the group consisting of non-metallic materials and low-iron, corrosion resistant alloys; and
   (c) neutralizing the product formed in step (b).

25. The process according to claim 24 comprising performing step (b) at a temperature of at least 91° C.

26. The process according to claim 25 wherein step (b) is performed at a temperature range of between about 91° C. and about 110° C.

27. The process according to claim 25 wherein step (b) is performed at a temperature range of between about 95° C. and about 105° C.

28. The process according to claim 24 wherein the bleaching agent is hydrogen peroxide.

29. The process according to claim 24 wherein the bleaching step (b) further comprises continuously refluxing the alcohol during bleaching and stripping gaseous by-products from the product formed during step (b) with said alcohol.

30. The process according to claim 29 including stripping water from the product formed during step (b) and replacing said water with an approximately equal amount of alcohol.

31. The process according to claim 24 wherein the alcohol is selected from the group consisting of primary alcohols having 1 to 4 carbon atoms, secondary alcohols having 3 to 4 carbon atoms, and mixtures thereof.

32. The process according to claim 31 wherein the alcohol is methanol.

33. The process according to claim 24 wherein the alcohol addition ranges between about 21 wt. % and about 40 wt. % based upon the crude sulfonic acid weight.

34. The process according to claim 24 further comprising continuously stripping oxygen and ethers after the bleaching step (b).

35. The process according to claim 24 wherein a liquid base is utilized for the neutralizing step (c).

36. The process according to claim 35 wherein the alcohol addition ranges between about 21 wt. % and about 40 wt. % based upon the crude sulfonic acid weight.

37. The process according to claim 35 wherein the liquid base is a sodium hydroxide solution.

38. The process according to claim 24 wherein a solid metal carbonate is utilized for the neutralizing step (c).

39. The process according to claim 38 wherein the alcohol addition ranges between about 21 wt. % and about 40 wt. % based upon the crude sulfonic acid weight.

40. The process according to claim 38 wherein the solid metal carbonate is sodium carbonate.

41. The process according to claim 24 further comprising reacting residual bleaching agents and organic peroxides from the product formed in step (b) with a reducing agent.

42. The process according to claim 41 wherein the reducing agent is selected from the group consisting of $SO_2$, salts of $SO_2$, acids of $SO_2$, and mixtures thereof.

43. The process according to claim 38 further comprising reacting residual bleaching agents and organic peroxides from the product formed in step (b) with a reducing agent during step (c).

44. A process for preparing a sulfonated fatty acid ester surfactant comprising:

(a) sulfonating a fatty acid ester thereby producing a crude sulfonic acid;

(b) reacting the crude sulfonic acid with a bleaching agent with the co-addition of at least 31 wt. % of an alcohol based upon the crude sulfonic acid weight, said alcohol selected from the group consisting of primary alcohols having 1 to 4 carbon atoms, secondary alcohols having 3 to 4 carbon atoms, and mixtures thereof; and (c) neutralizing the product formed in step (b).

45. The process according to claim 44 wherein said alcohol is methanol.

46. The process according to claim 44 wherein the bleaching agent is hydrogen peroxide.

47. The process according to claim 44 wherein the bleaching step (b) further comprises continuously refluxing the alcohol during bleaching and stripping gaseous by-products from the product formed during step (b) with said alcohol.

48. The process according to claim 47 including stripping water from the product formed during step (b) and replacing said water with an approximately equal amount of alcohol.

49. The process according to claim 44 wherein the alcohol addition ranges between 31 wt. % and about 40 wt. % based upon the crude sulfonic acid weight.

50. The process according to claim 44 further comprising continuously stripping oxygen and ethers after the bleaching step (b).

51. The process according to claim 44 wherein a liquid base is utilized for the neutralizing step (c).

52. The process according to claim 51 wherein the liquid base is a sodium hydroxide solution.

53. The process according to claim 44 wherein a solid metal carbonate is utilized for the neutralizing step (c).

54. The process according to claim 53 wherein the solid metal carbonate is sodium carbonate.

55. The process according to claim 44 further comprising reacting residual bleaching agents and organic peroxides from the product formed in step (b) with a reducing agent.

56. The process according to claim 55 wherein the reducing agent is selected from the group consisting of $SO_2$, salts of $SO_2$, acids of $SO_2$, and mixtures thereof.

57. The process according to claim 53 further comprising reacting residual bleaching agents and organic peroxides from the product formed in step (b) with a reducing agent during step (c).

58. In a process for neutralizing an organic acid, the improvement comprising:

performing the neutralization with a solid base in the presence of solvent in an amount sufficient to form a neutralization mixture in the form of one of a solution and a slurry, said solvent being predominantly alcohol.

59. The improvement according to claim 58 wherein the alcohol is selected from the group consisting of primary alcohols having 1 to 4 carbon atoms, secondary alcohols having 3 to 4 carbon atoms, and mixtures thereof.

60. The improvement according to claim 59 wherein the alcohol is selected from the group consisting of methanol and ethanol.

61. The improvement according to claim 58 wherein the amount of alcohol present during neutralization ranges between about 21 wt. % and about 40 wt. % based upon the organic acid weight.

62. The improvement according to claim 58 wherein a solid metal carbonate is utilized for neutralization.

63. The improvement according to claim 62 wherein the solid metal carbonate is sodium carbonate.

64. The improvement according to claim 58 wherein alcohol is removed and recovered for re-use.

65. The improvement according to claim 58 wherein the organic acid is bleached prior to neutralization and further comprising reacting residual bleaching agents and organic peroxides with a reducing agent.

* * * * *

UNITED STATES PATENT AND TRADEMARK OFFICE
CERTIFICATE OF CORRECTION

PATENT NO. : 5,587,500
DATED : December 24, 1996
INVENTOR : Keith D. HOVDA
ASSIGNEE : The Chemithon Corporation It is certified that error appears in the above-identified patent and that said Letters Patent is hereby corrected as shown below:

Column 4/Line 47:

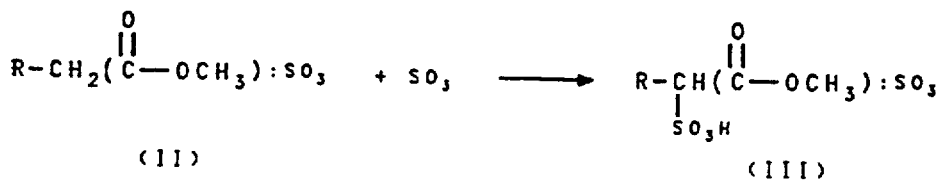

Column 4/Line 58:

Column 5/Line 23:

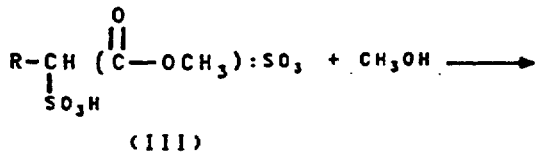

UNITED STATES PATENT AND TRADEMARK OFFICE
CERTIFICATE OF CORRECTION

PATENT NO. : 5,587,500
DATED : December 24, 1996
INVENTOR : Keith D. HOVDA
ASSIGNEE : The Chemithon Corporation It is certified that error appears in the above-identified patent and that said Letters Patent is hereby corrected as shown below:

Column 6/Line 3:

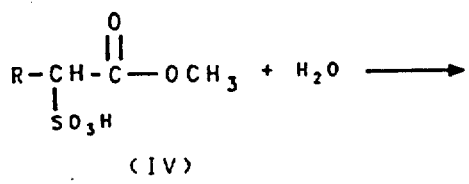

Column 6/Line 8:

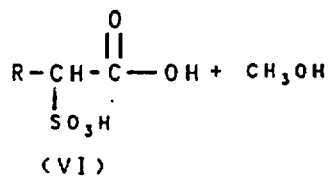

Column 6/Line 43:

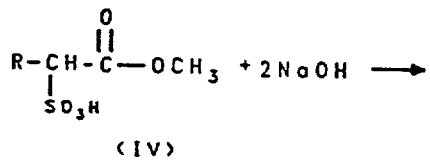

UNITED STATES PATENT AND TRADEMARK OFFICE
CERTIFICATE OF CORRECTION

PATENT NO. : 5,587,500
DATED : December 24, 1996
INVENTOR : Keith D. HOVDA
ASSIGNEE : The Chemithon Corporation It is certified that error appears in the above-identified patent and that said Letters Patent is hereby corrected as shown below:

Column 5/Line 28:

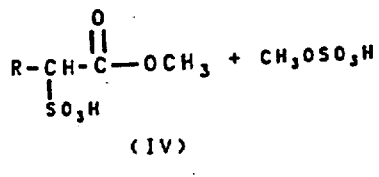

(IV)

Column 5/Line 42:

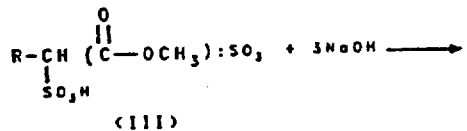

(III)

Column 5/Line 46:

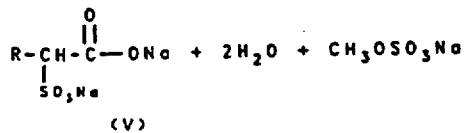

(V)

UNITED STATES PATENT AND TRADEMARK OFFICE
CERTIFICATE OF CORRECTION

PATENT NO. : 5,587,500
DATED : December 24, 1996
INVENTOR : Keith D. HOVDA
ASSIGNEE : The Chemithon Corporation It is certified that error appears in the above-identified patent and that said Letters Patent is hereby corrected as shown below:

Column 6/Line 48:

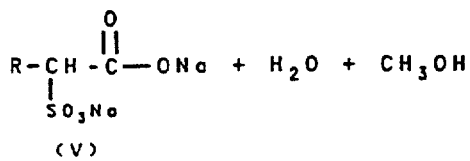

Column 7/Line 6:

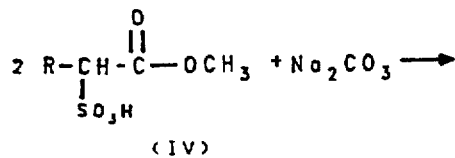

UNITED STATES PATENT AND TRADEMARK OFFICE
CERTIFICATE OF CORRECTION

PATENT NO. : 5,587,500
DATED : December 24, 1996
INVENTOR(S) : Keith D. HOVDA

The Chemithon Corporation

It is certified that error appears in the above-identified patent and that said Letters Patent is hereby corrected as shown below:

Column 7/Line 11:

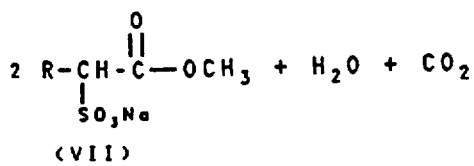

Signed and Sealed this

Twenty-fifth Day of November, 1997

Attest:

BRUCE LEHMAN

Attesting Officer    Commissioner of Patents and Trademarks